(12) United States Patent
Tehrani

(10) Patent No.: US 8,695,593 B2
(45) Date of Patent: Apr. 15, 2014

(54) WEANING AND DECISION SUPPORT SYSTEM FOR MECHANICAL VENTILATION

(76) Inventor: Fleur T. Tehrani, Anaheim, CA (US)

( * ) Notice: Subject to any disclaimer, the term of this patent is extended or adjusted under 35 U.S.C. 154(b) by 2169 days.

(21) Appl. No.: 11/841,806

(22) Filed: Aug. 20, 2007

(65) Prior Publication Data

US 2008/0236582 A1 Oct. 2, 2008

Related U.S. Application Data

(60) Provisional application No. 60/909,416, filed on Mar. 31, 2007.

(51) Int. Cl.
*A61M 16/00* (2006.01)

(52) U.S. Cl.
USPC ............ 128/204.23; 128/204.18; 128/204.21; 128/204.26

(58) Field of Classification Search
USPC ............. 128/200.24, 204.18, 204.21, 204.22, 128/204.23, 204.26; 600/529–543
See application file for complete search history.

(56) References Cited

U.S. PATENT DOCUMENTS

| | | | |
|---|---|---|---|
| 2,414,747 A | 1/1947 | Kirschbaum | |
| 3,734,091 A | 5/1973 | Taplin | |
| 3,967,619 A | 7/1976 | Story et al. | |
| 4,121,578 A | 10/1978 | Torzala | |
| 4,163,450 A | 8/1979 | Kirk et al. | |
| 4,326,513 A | 4/1982 | Schulz | |
| 4,448,192 A | 5/1984 | Stawitcke et al. | |
| 4,584,996 A | 4/1986 | Blum | |
| 4,665,911 A | 5/1987 | Williams et al. | |
| 4,773,411 A | 9/1988 | Downs | |
| 4,889,116 A | 12/1989 | Taube | |
| 4,986,268 A | 1/1991 | Tehrani | |
| 5,103,814 A | 4/1992 | Maher | |
| 5,315,990 A | 5/1994 | Mondry | |
| 5,365,922 A | 11/1994 | Raemer | |
| 5,388,575 A | 2/1995 | Taube | |
| 5,682,877 A | 11/1997 | Mondry | |
| 5,692,497 A | 12/1997 | Schnitzer et al. | |
| 5,752,509 A | 5/1998 | Lachmann et al. | |
| 5,931,160 A | 8/1999 | Gilmore et al. | |
| 6,148,814 A | 11/2000 | Clemmer et al. | |
| 6,158,432 A | 12/2000 | Biondi et al. | |
| 6,269,812 B1 * | 8/2001 | Wallace et al. | ........ 128/205.23 |
| 6,273,088 B1 | 8/2001 | Hillsman | |
| 6,325,978 B1 | 12/2001 | Labuda et al. | |
| 6,371,114 B1 | 4/2002 | Schmidt et al. | |
| 6,390,091 B1 | 5/2002 | Banner et al. | |
| 6,463,930 B2 | 10/2002 | Biondi et al. | |
| 6,512,938 B2 | 1/2003 | Claure et al. | |

(Continued)

OTHER PUBLICATIONS

Y. Mitamura, T. Mikami, H. Sugawara, and C. Yoshimoto, "An Optimally Controlled Respirator," *IEEE Transactions on Biomedical Engineering*, BME-18, pp. 330-337, 1971.

(Continued)

*Primary Examiner* — Justine Yu
*Assistant Examiner* — LaToya M Louis
(74) *Attorney, Agent, or Firm* — One LLP

(57) ABSTRACT

A system for mechanical ventilation treatment is described. In one embodiment the system provides advice on treatment and/or weaning of patients from mechanical ventilation based on the patient's conditions. In another embodiment the system includes apparatus to monitor and analyze the patient's data and data from the mechanical ventilator and controls the ventilator automatically.

67 Claims, 10 Drawing Sheets

(56) References Cited

U.S. PATENT DOCUMENTS

| | | | |
|---|---|---|---|
| 6,532,958 | B1 | 3/2003 | Buan et al. |
| 6,561,187 | B2 | 5/2003 | Schmidt et al. |
| 6,578,575 | B1 | 6/2003 | Jonson |
| 6,584,973 | B1 | 7/2003 | Biondi et al. |
| 6,668,829 | B2 | 12/2003 | Biondi et al. |
| 6,671,529 | B2 | 12/2003 | Claure et al. |
| 6,796,305 | B1 | 9/2004 | Banner et al. |
| 6,820,618 | B2 | 11/2004 | Banner et al. |
| 7,017,574 | B2 | 3/2006 | Biondi et al. |
| 7,066,173 | B2* | 6/2006 | Banner et al. ............ 128/204.23 |
| 7,210,478 | B2 | 5/2007 | Banner et al. |
| 2001/0004893 | A1 | 6/2001 | Biondi et al. |
| 2002/0072659 | A1 | 6/2002 | Claure et al. |
| 2003/0010339 | A1* | 1/2003 | Banner et al. ............ 128/204.18 |
| 2003/0037786 | A1 | 2/2003 | Biondi et al. |
| 2003/0078480 | A1 | 4/2003 | Claure et al. |
| 2003/0111078 | A1 | 6/2003 | Habashi |
| 2005/0051167 | A1 | 3/2005 | Biondi et al. |
| 2005/0109340 | A1 | 5/2005 | Tehrani |
| 2005/0205093 | A1* | 9/2005 | Jabour ..................... 128/204.23 |
| 2006/0162727 | A1 | 7/2006 | Biondi et al. |

OTHER PUBLICATIONS

J.R. Coles, W.A. Brown, and D.G. Lampard, "Computer Control of Ventilation and Anesthesia," *Medical and Biological Engineering*, vol. 11, pp. 262-267, 1973.

Y. Mitamura, T. Mikami, K. Yamamoto, and K. Mimura, "A Dual Control System for Assisting Respiration," *Medical and Biological Engineering*, vol. 13, No. 6, pp. 846-854, 1975.

A.M. Hewlett, A.S. Platt, V.G. Terry, "Mandatory Minute Volume," *Anesthesia*, vol. 32, pp. 163-169, 1977.

K.B. Ohlson, D.R. Westenskow, and W.S. Jordan, "A Microprocessor Based Feedback Controller for Mechanical Ventilation," *Annals of Biomedical Engineering*, vol. 10, pp. 35-48, 1982.

W. F. Fincham, and F. T. Tehrani, "A mathematical model of the human respiratory system," *Journal of Biomedical Engineering*, vol. 5, pp. 125-133, 1983.

F.W. Chapman, J.C. Newell, and R.J. Roy, "A Feedback Controller for Ventilatory Therapy," *Annals of Biomedical Engineering*, vol. 13, pp. 359-372, 1985.

M.H. Giard, F.O. Bertrand, D. Robert, and J. Pernier, "An Algorithm for Automatic Control of $O_2$ and $CO_2$ in artificial ventilation," *IEEE Transactions on Biomedical Engineering*, vol. BME-32, No. 9, pp. 658-667, 1985.

T. D. East, K. P. Adriano, N. L. Pace, Computer-controlled optimization of positive end-expiratory pressure, *Critical Care* Medicine, vol. 14, No. 9, pp. 792-797, 1986.

T. D. East, J. C. C. M. Veen, T. A. Jonker, N. L. Pace, and S. McJames, "Computer-controlled positive end-expiratory pressure titration for effective oxygenation without frequent blood gases." *Critical Care Medicine*, vol. 16, No. 3, pp. 252-257, 1988.

R. Rudowski, L. Skreta, S. Baehrendtz, A. Bokliden, and G. Matell, "Lung function analysis and optimization during artificial ventilation. A personal computer-based system." *Computer Methods and Programs in Biomedicine*, vol. 31, pp. 33-42, 1990.

R. Rudowski, A. Bokliden, A. Carstensen, H. Gill, U. Ludwigs, G. Matell, "Multivariable optimization of mechanical ventilation. A linear programming approach." *International Journal of Clinical Monitoring and Computing*. vol. 8, pp. 107-115, 1991.

T. D. East, C. R. Tolle, S. McJames, R. M. Farrell, J. X. Brunner, "A non-linear closed-loop controller for oxygenation based on a clinically proven fifth dimensional quality surface," *Anesthesiology*, vol. 75, A468, 1991.

M. Dojat, L. Brochard, F. Lemaire, and A. Harf, "A knowledge-based system for assisted ventilation of patients in intensive care units," *International Journal of Clinical Monitoring and Computing*, vol. 9, pp. 239-250, 1992.

F. T. Tehrani, "Mathematical analysis and computer simulation of the respiratory system in the newborn infant," *IEEE Transactions on Biomedical Engineering*, vol. 40, No. 5, pp. 475-481, 1993.

D. M. Linton, J. X. Brunner, and T. P. Laubscher, "Continuous use of an adaptive lung ventilation controller in critically ill patients in a multi-disciplinary intensive care unit," *South African Medical Journal*, vol. 85, pp. 432-435, 1995.

T. Fernando, J. Cade, and J. Packer, "Automatic control of arterial carbon dioxide tension in mechanically ventilated patients," *IEEE Transactions on Information Technology in Biomedicine*, vol. 6(4), pp. 269-276, 2002.

T. Lo, F. T. Tehrani, M. Rogers, M. Lum, T. Malinowski, S. Afuwape, M. Terry, B. Grundl, "A dual closed-loop controller for mechanical ventilation," (abstract), *American Journal of Respiratory and Critical Care Medicine*, vol. 165(8), supplement, part 2, Apr. 2002.

F. T. Tehrani, M. Rogers, T. Lo, T. Malinowski, S. Afuwape, M. Lum, B. Grundl, and M. Terry, "A dual closed loop control system for mechanical ventilation," *Journal of Clinical Monitoring and Computing.*, vol. 18, pp. 111-129, 2004.

J. R. Anderson, and T. D. East, "A closed-loop controller for mechanical ventilation of patients with ARDS," *Biomedical Sciences Instrumentation; Proceedings of the Annual Rocky Mountain Bioengineering Symposium*, vol. 38, pp. 289-294, 2002.

T. P. Laubscher, W. Heinrichs, N. Weiler, G. Hartmann, and J. X. Brunner, "An adaptive lung ventilation controller," *IEEE Transactions on Biomedical Engineering*, vol. 41, No. 1, pp. 51-59, 1994.

D. M. Linton, P. D. Potgieter, S. Davis, A. T. J. Fourie, J. X. Brunner, T. P. Laubscher, "Automatic weaning from mechanical ventilation using an adaptive lung ventilation controller," *Chest*, vol. 106, No. 6, pp. 1843-1850, 1994.

T. L. Fernando, J. S. Packer, and J. F. Cade, "A closed-loop system for controlling blood oxygen and carbon dioxide levels in mechanically ventilated patients," *Control Eng. Practice*, vol. 3, No. 10, pp. 1433-1440, 1995.

A. B. Otis, W. O. Fenn, and H. Rahn, "Mechanics of breathing in man," *Journal of Applied Physiology*, vol. 2, pp. 592-607, 1950.

I. R. Beddis, P. Collins, N. M. Levy, S. Godfrey, and M. Silverman, "New technique for servo-control of arterial oxygen tension in preterm infants," *Archives of Disease in Childhood*, vol. 54, pp. 278-280, 1979.

A. Sano, and M. Kikucki, "Adaptive control of arterial oxygen pressure of newborn infants under incubator oxygen treatments," *Proceedings of IEE*, vol. 132(Pt. D., No. 5), pp. 205-211, 1985.

C. Yu, W. G. He, J. M. So, R. Roy, H. Kaufman, and J. C. Newell, "Improvement in arterial oxygen control using multiple model adaptive control procedures," *IEEE Transactions on Biomedical Engineering*, BME-34, No. 8, pp. 567-574, 1987.

R. E. Dugdale, R. G. Cameron, and G. T. Lealman, "Closed-loop control of the partial pressure of arterial oxygen in neonates," *Clinical Physics and Physiological Measurement*, vol. 9, No. 4, pp. 291-305, 1988.

P. E. Morozoff, and R. W. Evans, "Closed loop control of $S_{aO2}$ in the neonate," *Biomedical Instrumentation and Technology*, vol. 26, pp. 117-123, 1992.

F. T. Tehrani, "A microcomputer oxygen control system for ventilatory therapy," *Annals of Biomedical Engineering*, vol. 20, No. 5, pp. 547-558, 1992.

J. R. Anderson, T. D. East, J. Coombs, T. Clemmer, J. Orme, L. Weaver, "Clinical trial of a non-linear closed-loop controller for oxygenation during ARDS," *Critical Care Medicine*, vol. 22, A188, Jan. 1994.

F. T. Tehrani, and A. R. Bazar, "A feedback controller for supplemental oxygen treatment of newborn infants: a simulation study," *Medical Engineering and Physics*, vol. 16, pp. 329-333, 1994.

D. B. Waisel, J. C. Fackler, J. X. Brunner, I. Kohane, "PEFIOS: An expert closed-loop oxygenation algorithm," *MEDINFO 95*, Proceedings of the 8th World Congress, pp. 1132-1136, 1995.

D. B. Raemer, X. Ji, and G. P. Topulos, "$F_{IX}$ controller: an instrument to automatically adjust inspired oxygen fraction using feedback control from a pulse oximeter," *Journal of Clinical Monitoring*, vol. 13, pp. 91-101, 1997.

F. T. Tehrani, "A control system for oxygen therapy of premature infants," in *The Proceedings of the 23rd Annual International Conference of IEEE Engineering in Medicine and Biology Society*, vol. 23, No. 2, pp. 2059-2062, Oct. 2001.

(56) References Cited

OTHER PUBLICATIONS

F. T. Tehrani, M. Rogers, T. Lo, T. Malinowski, S. Afuwape, M. Lum, B. Grundl, and M. Terry, "Closed-loop control of the inspired fraction of oxygen in mechanical ventilation," *Journal of Clinical Monitoring and Computing*, vol. 17, No. 6, pp. 367-376, 2002.

P. Miller, "Goal-directed critiquing by computer: ventilator management," *Computers and Biomedical Research*, vol. 18, pp. 422-438, 1985.

W. A. Carlo, L. Pacifico, R. L. Chatburn, and A. A. Fanaroff, "Efficacy of computer-assisted management of respiratory failure in neonates," *Pediatrics*, vol. 78, No. 1, pp. 139-143, 1986.

C. Hernandez, V. Moret, B. Arcay, and R. C. Hermida, "Weaning from mechanical ventilation using a prototype closed-loop system," *Microcomputer Applications*, vol. 7, No. 3, pp. 128-130, 1988.

C. Hernandez-Sande, V. Moret-Bonillo and A. Alonso-Betanzos, ESTER: An expert system for management of respiratory weaning therapy, *IEEE Transactions on Biomedical Engineering*, vol. 36, pp. 559-564, 1989.

D. F. Sittig, N. L. Pace, R. M. Gardner, E. Beck, and A. H. Morris, "Implementation of a computerized patient advice system using the HELP clinical information system," *Computers and Biomedical Research*, vol. 22, pp. 474-487, 1989.

J. H. Strickland Jr., and J. H. Hassan, "A computer-controlled weaning system," *Chest*, vol. 100, pp. 1096-1099, 1991.

M. Dojat, A. Harf, D. Touchard, F. Lemaire, and L. Brochard, "Clinical evaluation of a computer-controlled pressure support mode," *American Journal of Respiratory and Critical Care Medicine*, vol. 161, pp. 1161-1166, 2000.

L. Bouadma, F. Lellouche, B. Cabello, S. Taille, J. Mancebo, M. Dojat, and L. Brochard, "Computer-driven management of prolonged mechanical ventilation and weaning: a pilot study," *Intensive Care Medicine*, vol. 31, pp. 1446-1450, 2005.

G. W. Rutledge, G. E. Thomsen, B. R. Fan, M. A. Tovar, J. X. Polaschek, I. A. Beinlich, L. B. Sheiner, and L. M. Fagan, "The design and implementation of a ventilator-management advisor," *Artificial Intelligence in Medicine*, vol. 5, pp. 67-82, 1993.

J. H. Strickland, Jr., and J. H. Hassan, "A computer-controlled ventilator weaning system," *Chest*, vol. 103, No. 4, pp. 1220-1225, 1993.

B. A. McKinley, F. A. Moore, R. M. Sailors, C. S. Cocanour, A. Marquez, R. K. Wright, A. S. Tonnesen, C. J. Wallace, A. H. Morris, and T. D. East, "Computerized decision support for mechanical ventilation of trauma induced ARDS: results of a randomized clinical trial," *Journal of Trauma*, vol. 50, No. 3, pp. 415-425, 2001.

F. T. Tehrani, "Automatic control of an artificial respirator," *Proceedings of the Annual International Conference of IEEE Engineering in Medicine and Biology Society*, vol. 13, pp. 1738-1739, 1991.

R. G. Brower, A. Morris, N. MacIntyre, M. A. Matthay, D. Hayden, T. Thompson, T. Clemmer, P. Lanken, and D. Schoenfeld, "Effects of recruitment maneuvers in patients with acute lung injury and acute respiratory distress syndrome ventilated with high positive end-expiratory pressure," *Critical Care Medicine*, vol. 31, No. 11, pp. 2592-2597, 2003.

S. Mersmann, and K. Kuck, "SmartCare-Optimizing workflow processes in critical care through automation," *Journal of Clinical Monitoring and Computing*, vol. 20, pp. 119-120, 2006.

S. E Rees, C. Allerod, D. Murley, Y. Zhao, B. W. Smith, S. Kjargaard, P. Thorgaard, and S. Andreassen, "Using physiological models and decision theory for selecting appropriate ventilator settings," *Journal of Clinical Monitoring and Computing*, vol. 20, pp. 421-429, 2006.

* cited by examiner

US 8,695,593 B2

WEANING AND DECISION SUPPORT SYSTEM FOR MECHANICAL VENTILATION

CROSS REFERENCE TO RELATED APPLICATIONS

This application claims the benefit of U.S. Provisional Patent Application No. 60/909,416, filed Mar. 31, 2007.

FIELD OF THE INVENTION

This invention relates generally to technology for weaning and treatment of patients on mechanical ventilation. More specifically, the invention relates to a method and apparatus for open or closed loop control of a mechanical ventilator through monitoring and analysis of patient and ventilator input data.

BACKGROUND OF THE INVENTION

Mechanical ventilation is one of the most widely used techniques of treatment of patients particularly in the intensive care units of hospitals. Proper management of patients on the ventilator and safe and timely weaning and extubation of patients are the objectives that serve as key factors in expediting recovery and reducing the mortality and morbidity risks associated with the treatment. A system that can provide expert advice to clinicians for such treatment and that can automatically and safely wean the patients from the ventilator can be a valuable tool in achieving these objectives.

Attempts to provide expert advice for mechanical ventilation have been described. There have been systems for treatment of ARDS patients only. See D. F. Sittig et al., "Implementation of a Computerized Patient Advice System Using the HELP Clinical Information System," Computers and Biomedical Research, Vol. 22, pages 474-487, 1989. There have also been expert and control systems developed for use in pressure support mechanical ventilation mode only. See M. Dojat et al., "Evaluation of a Knowledge-Based System Providing Ventilatory Management and Decision for Extubation," American Journal of Respiratory and Critical Care Medicine, Vol. 153, pages 997-1004, 1996.

However, the previous techniques were developed for use in specific ventilation modes or were designed for specific groups of patients. What is needed is an expert and control system for a mechanical ventilator that may be customized according to patient needs to address a broader field of respiratory conditions and therapies.

SUMMARY OF THE INVENTION

A method of providing treatment advice for patients on mechanical ventilation includes steps of analyzing patient's and ventilator's data, computing and recommending optimal ventilatory requirements, suggesting on whether weaning should be started, continued or stopped, and providing appropriate warning messages when necessary. A system can also be implemented by using an apparatus including sensors for continuous monitoring of patient data.

The system may use data representative of carbon dioxide and oxygen levels of the patient, the respiratory mechanics data such as airway resistance and respiratory compliance, the patient's ideal body weight and temperature, the settings on the ventilator such as tidal volume, respiratory rate, positive end-expiratory pressure, the inspiratory to expiratory time ratio, the inspired oxygen concentration, the maximum allowed levels of volume and pressure on the ventilator for the patient, measured tidal volume and the spontaneous breathing rate of the patient as well as the mode of the mechanical ventilator.

The system is designed to help regulate patient's arterial blood gases within an acceptable range, provide patient's data over time to the clinician, and to expedite weaning from the ventilator in a safe and timely manner. It provides advice on how much ventilation the patient requires and recommends ventilator settings to minimize the respiratory work rate. It determines the optimal levels of inspired oxygen fraction and positive end-expiratory pressure for the patient. It provides advice on other settings of the ventilator such as the inspiratory to expiratory time ratio and warns the clinician of any untoward condition of the patient. It recommends whether weaning should be started, continued or stopped. It has the capability of providing advice in a wide range of ventilation modes and for different patients on mechanical ventilation.

A system of the invention can also be implemented by using an apparatus including sensors for continuous monitoring of patient data. The system can provide automatic control of the ventilator and automatic weaning from the ventilator. This embodiment includes an apparatus for monitoring and analysis of the required data. The apparatus may include a computing system, digital readable memory coupled to the computing system, and transducers providing input signals to the computing system that may represent data such as airway resistance, respiratory compliance, spontaneous breathing rate, and measured tidal volume. Control of the ventilator may be achieved by providing the control signals to the ventilator automatically. This embodiment of the invention can be used for automatic weaning of the patient from the ventilator. The automatic weaning procedure will continue until the patient is ready for extubation, or if patient's conditions deteriorate, the system automatically increases the ventilator's support for the patient and generates a warning message to the clinician.

BRIEF DESCRIPTION OF THE DRAWINGS

For the purpose of illustrating the invention, a presently preferred form of the invention is shown in the drawings. However, it is understood that this invention is not limited to the precise arrangements and instrumentalities shown.

DETAILED DESCRIPTION

The present invention is designed for a wide range of patients and is not limited to any specific mode of ventilation. Unlike previous rule-based techniques, a system or method according to the invention operates, or derives many of its rules, on the basis of the conditions of individual patients. Therefore the system or method is quite responsive to the individual patient's bodily requirements. A system or method according to the invention may be used to achieve either open loop or closed loop control. In open loop control, a clinician may use the invention as an expert system or decision-support system, and may manually adjust or operate a mechanical ventilator based on output automatically provided by the decision-support system. In the closed loop scenario, the invention may provide a fully automatic control system for monitoring and operating the mechanical ventilator, while still allowing for a possible manual override by the clinician.

Figure 1:
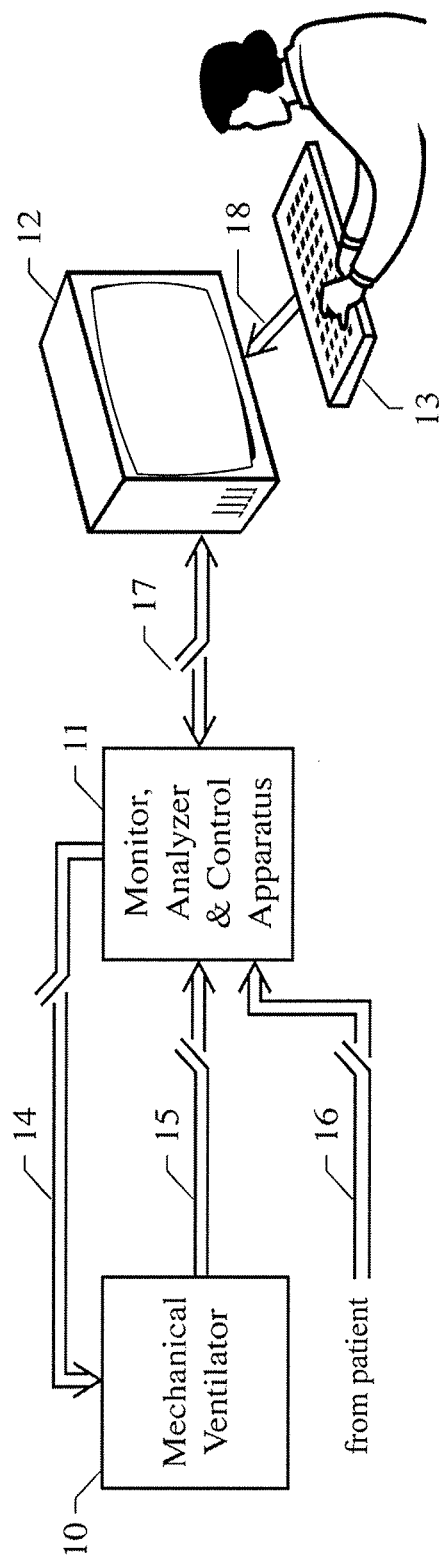
FIG. 1 is a block diagram depicting general applications of the invention.

Referring to the drawings, wherein like numerals represent like elements, there is illustrated in FIG. 1 a block diagram depicting general application of the invention. Data from the mechanical ventilator designated as 10 is provided via switched lines 15 to the Monitor, Analyzer, and Control apparatus 11. The switch in lines 15 is closed when data from the ventilator is sent automatically to apparatus 11. Apparatus 11 also receives patient data from one or more transducers through lines 16. Apparatus 11 sends outputs to computer 12 and communicates back and forth with computer 12 through switched lines 17 which preferably represent an RS232 or USB communication port. The control outputs of apparatus 11 are provided through switched lines 14 to mechanical ventilator 10 when the invention is used to automatically control the ventilator.

Switches in switched lines 14, 15, 16, and 17 may be manual or automatic switches. If automatic switches are used, they may include automatic switching means, such as relays, transistors, logic gates, and other solid state devices, and may be physically located at mechanical ventilator 10, apparatus 11, or computer 12, as desired. In another embodiment, one or more of switched lines 14, 15, 16, and 17 may represent a wireless connection.

Whether control is manual or automatic, a user interface 13 may be provided to allow a human user or clinician to enter data into computer 12 through a communication line 18. User interface 13 may be a keyboard, mouse, touchscreen, microphone, or other input device.

Computer 12 may be any computing system having a processor coupled to memory, and may include operating system software. Computer 12 may be or may include a customized digital controller such as an FPGA or ASIC or other processor programmed to execute the specific algorithms or methods of the present invention as disclosed herein, or computer 12 may be a personal computer system such as a desktop or laptop unit running an operating system such as Windows, Mac OS, Unix or Linux, and also having loaded in its memory a custom software application for executing the algorithms or methods of the present invention. In one embodiment, computer 12 may include a display unit such as a CRT or LCD monitor. The display unit may display options provided to a clinician by the custom software, and may display data received from a patient, data received from mechanical ventilator 10, data received from apparatus 11 such as instructions or warnings, or data input by the clinician through user interface 13.

The human operator may control the system using the computer 12 and user interface 13. At least three preferred modes of application of this invention may be recognized: (i) Decision Support mode, (ii) Open Loop manual mode, and (iii) Closed Loop automatic mode.

In Decision Support mode, the system is installed on computer 12 and the invention is used as a decision support tool. Patient and ventilator data are input to the system via user interface 13 by the human operator. Apparatus 111 is not needed in this mode and is not used. Adjustments of the ventilator 10 are done manually by the human operator.

In Open Loop manual mode, the system is installed on either computer 12 or on a processor incorporated in apparatus 11 that receives data from ventilator 10 and the patient on lines 15 and 16, respectively. In this mode, the human operator controls the ventilator 10 manually. There is no automatic control of ventilator 10 by the system of the invention and lines 14 are open.

In Closed Loop automatic mode, the system is installed on either computer 12 or on a processor incorporated in apparatus 11 that receives data from the ventilator 10 and the patient on lines 15 and 16, respectively. Ventilator 10 is controlled automatically by the invention through preferably lines 14. The human operator supervises the system and can change the data or intervene at any time by using computer 12 and user interface 13. One of the applications of this mode is in automatic weaning of the patient from the ventilator. The control outputs to ventilator 10 are updated automatically at predefined intervals and weaning is continued until the patient is ready for extubation or needs to have increased ventilatory support again in which case the system generates a warning message to the clinician and increases the level of support by ventilator 10.

Figure 2:
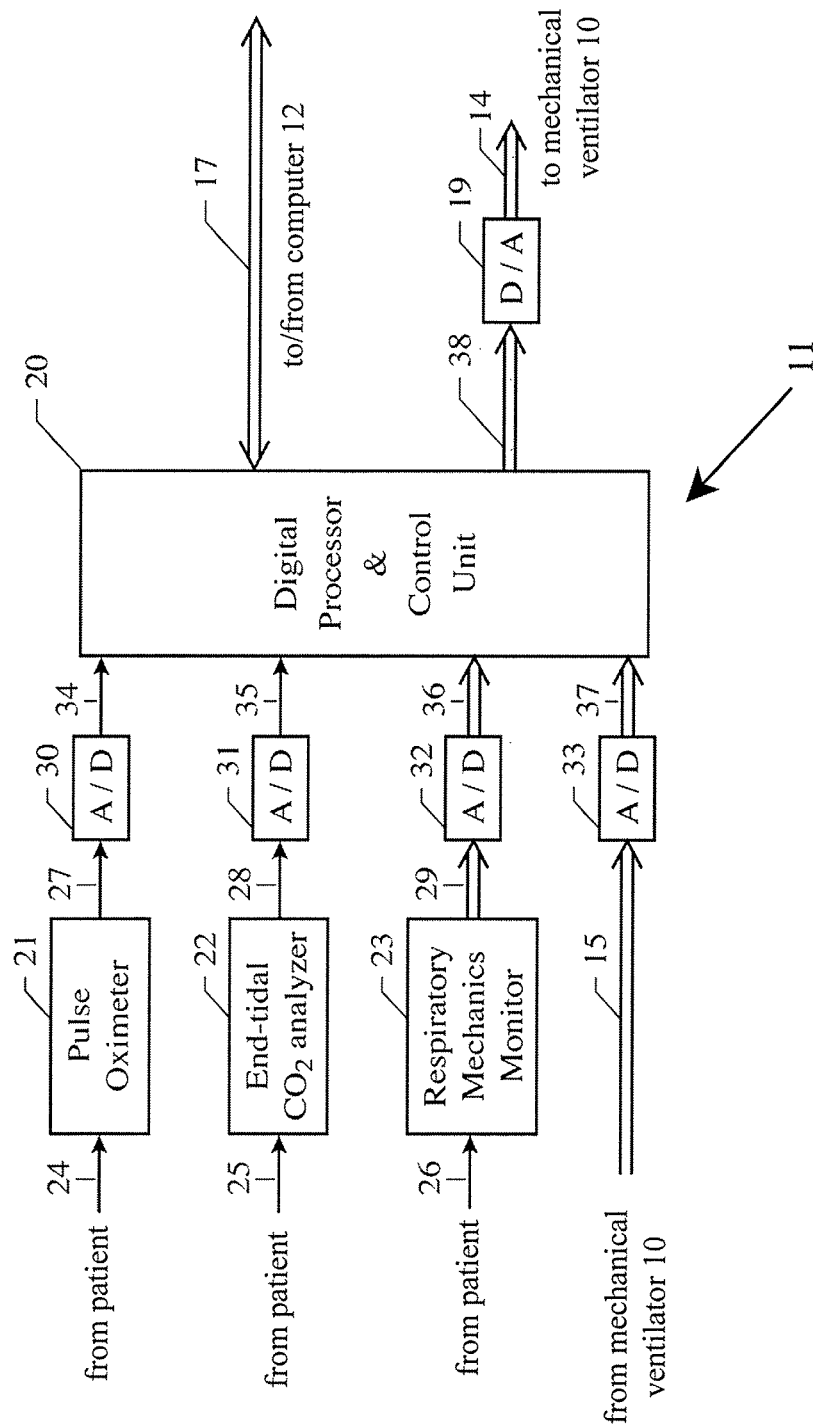
FIG. 2 is a block diagram of a Monitor, Analyzer, and Control Apparatus according to one embodiment of the invention.

FIG. 2 shows a block diagram of the preferred Monitor, Analyzer, and Control apparatus 11. It includes a Digital Processor and Control Unit 20, hereinafter control unit 20. This unit may have one or more digital controllers which may preferably be Micromint Brand BCC 52 BASIC controllers. The input data from ventilator 10 is applied to an analog to digital converter (A/D) board 33 through lines 15. The outputs of A/D 33 are applied to control unit 20 through lines 37. This data may include ventilatory data such as set tidal volume, measured tidal volume, respiratory rate, the spontaneous breathing rate, the peak inspiratory pressure, the positive end-expiratory pressure, the inspiratory to expiratory time ratio, the maximum allowed levels of volume and pressure, and data indicative of the mode of ventilation.

Patient oxygen level at 24 is preferably measured by using a transducer such as a pulse oximeter 21. Output 27 of pulse oximeter 21 is applied to an A/D converter 30, and the digital output from A/D converter 30 is applied to control unit 20 at line 34. The patient's $CO_2$ level at 25 may be measured by using a transducer such as an end-tidal $CO_2$ analyzer 22. Output 28 of analyzer 22 is applied to an A/D converter 31, and the digital output from A/D converter 31 is provided at line 35 to control unit 20. The patient's respiratory compliance and airway resistance may be measured by using a transducer such as a respiratory mechanics monitor 23, which receives its inputs from the patient at 26 and provides its outputs at line 29 to an A/D board 32. The outputs of A/D board 32 are applied at line 36 to control unit 20. The control unit 20 communicates with computer 12 through a communication link 17, which is preferably RS232 or USB. If the system is used for automatic control of the ventilator, such as in a closed loop automatic mode, the output of control unit 20 may be applied at line 38 to one or more D/A converters 19, and the outputs of D/A converters 19 may be applied to ventilator 10 preferably through lines 14 as shown.

It should be noted that if the system is installed on computer 12 and computer 12 is equipped with a software package such as LabView for data collection and analysis, the system inputs can be applied to computer 12 and the digital processor and control unit 20 may not be needed. Also, if the Monitor, Analyzer, and Control Apparatus 11 is incorporated in the Mechanical Ventilator 10, A/D boards 33 and D/A boards 19 may not be needed. It is also clear that apparatus 11 may not be needed if the system is installed on computer 12 and all the controls and adjustments are done by a human operator.

Figure 3:
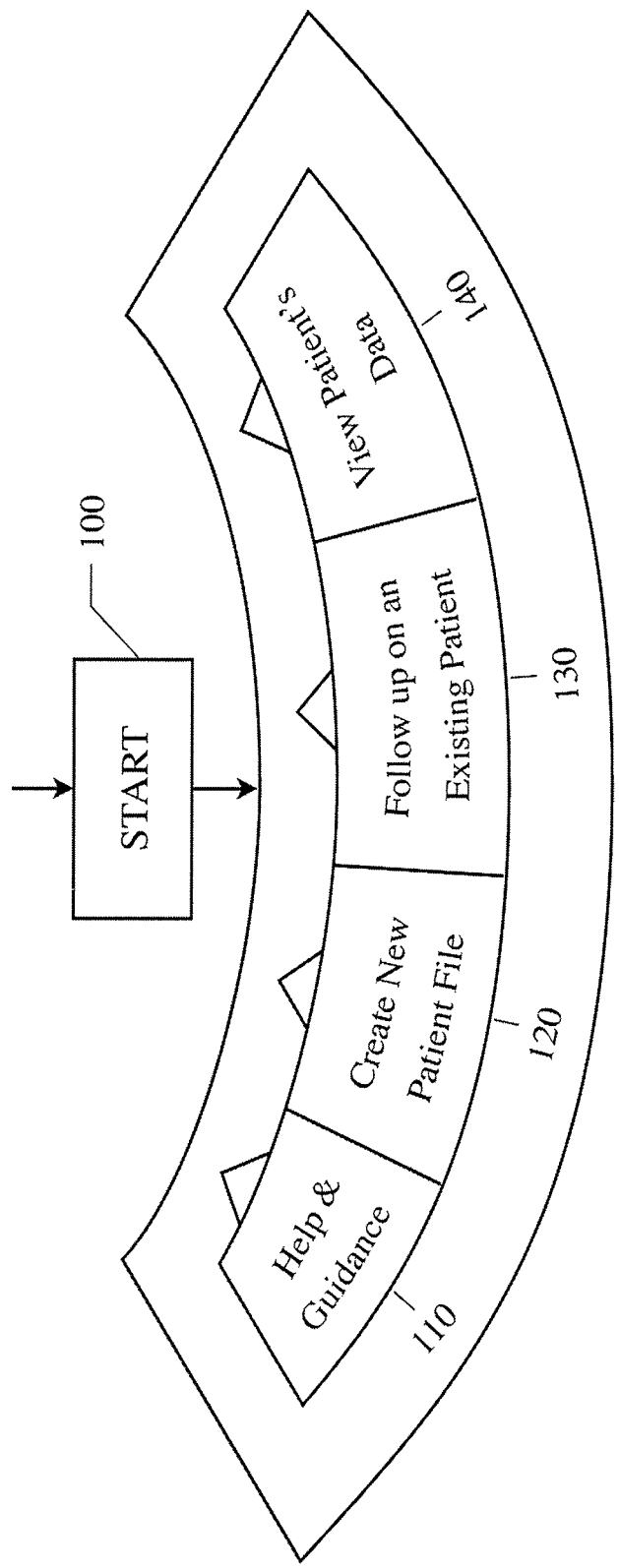
FIG. 3 shows a virtual switch board displayed on a computer screen that provides a user with initial options for operating software according to the invention.
Figure 4A:
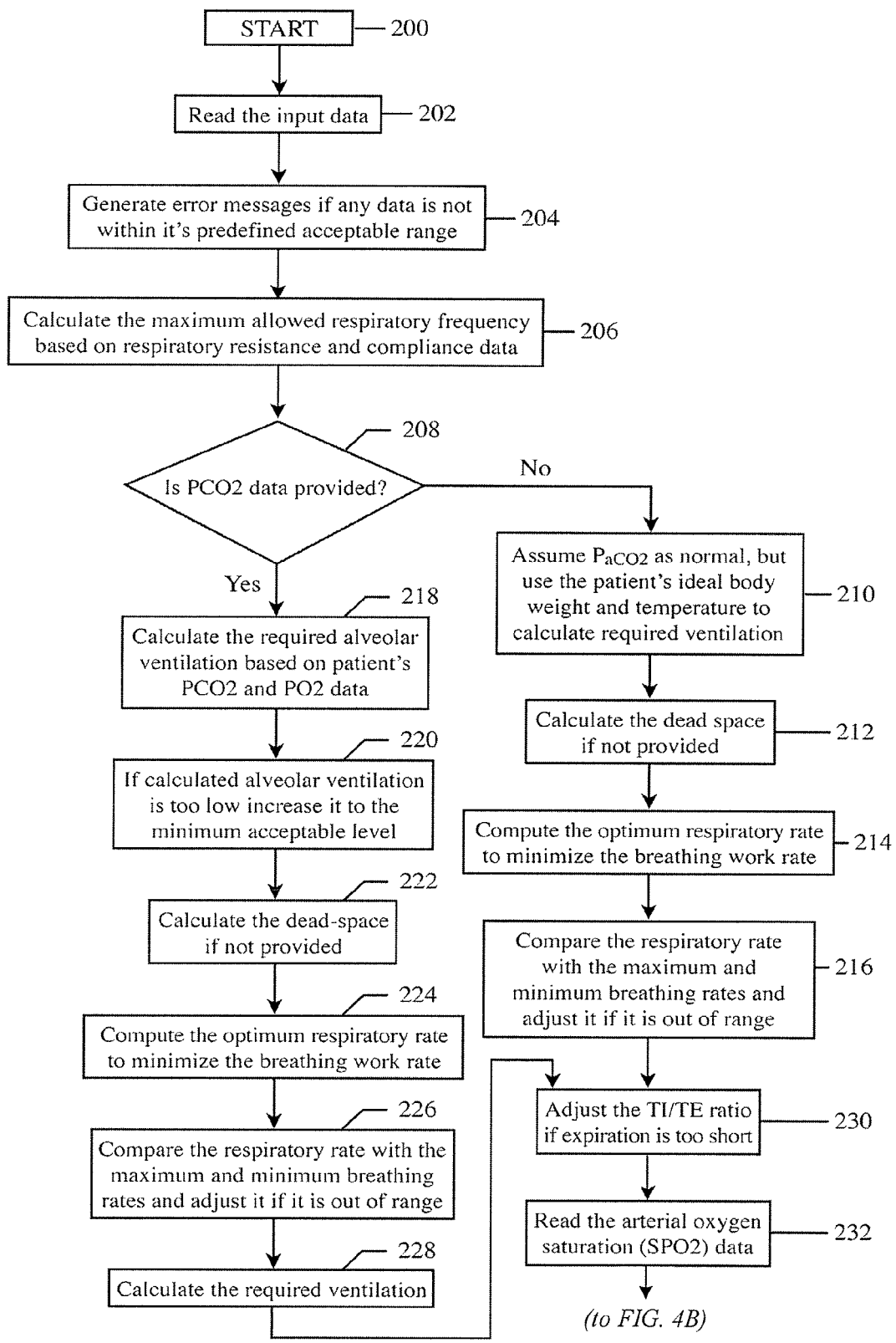
FIGS. 4A-4E are a flow chart illustrating one embodiment of a method according to the invention, including a preferred sequence of steps executable by a programmable system according to the invention.
Figure 4B:
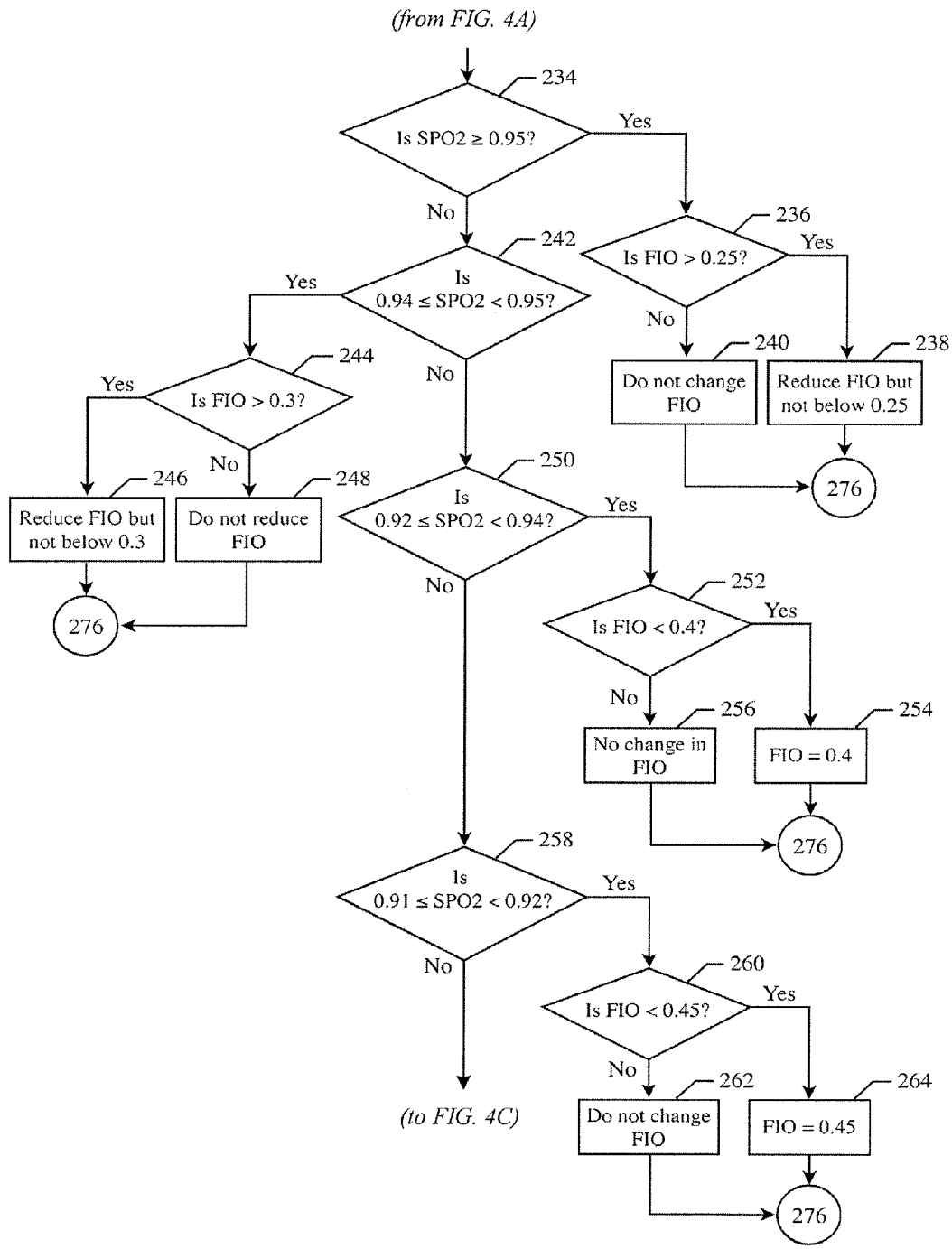
Figure 4C:
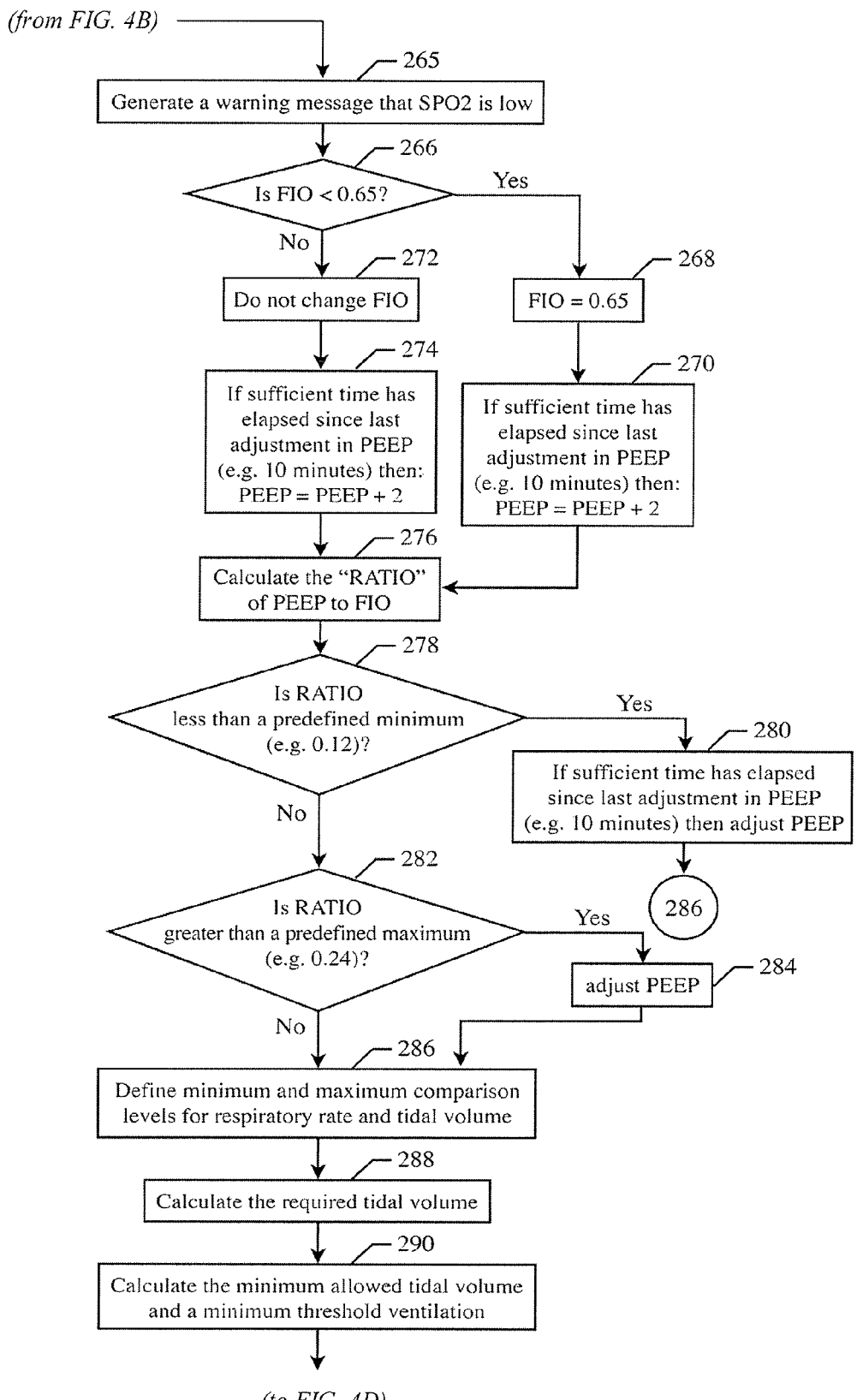
Figure 4D:
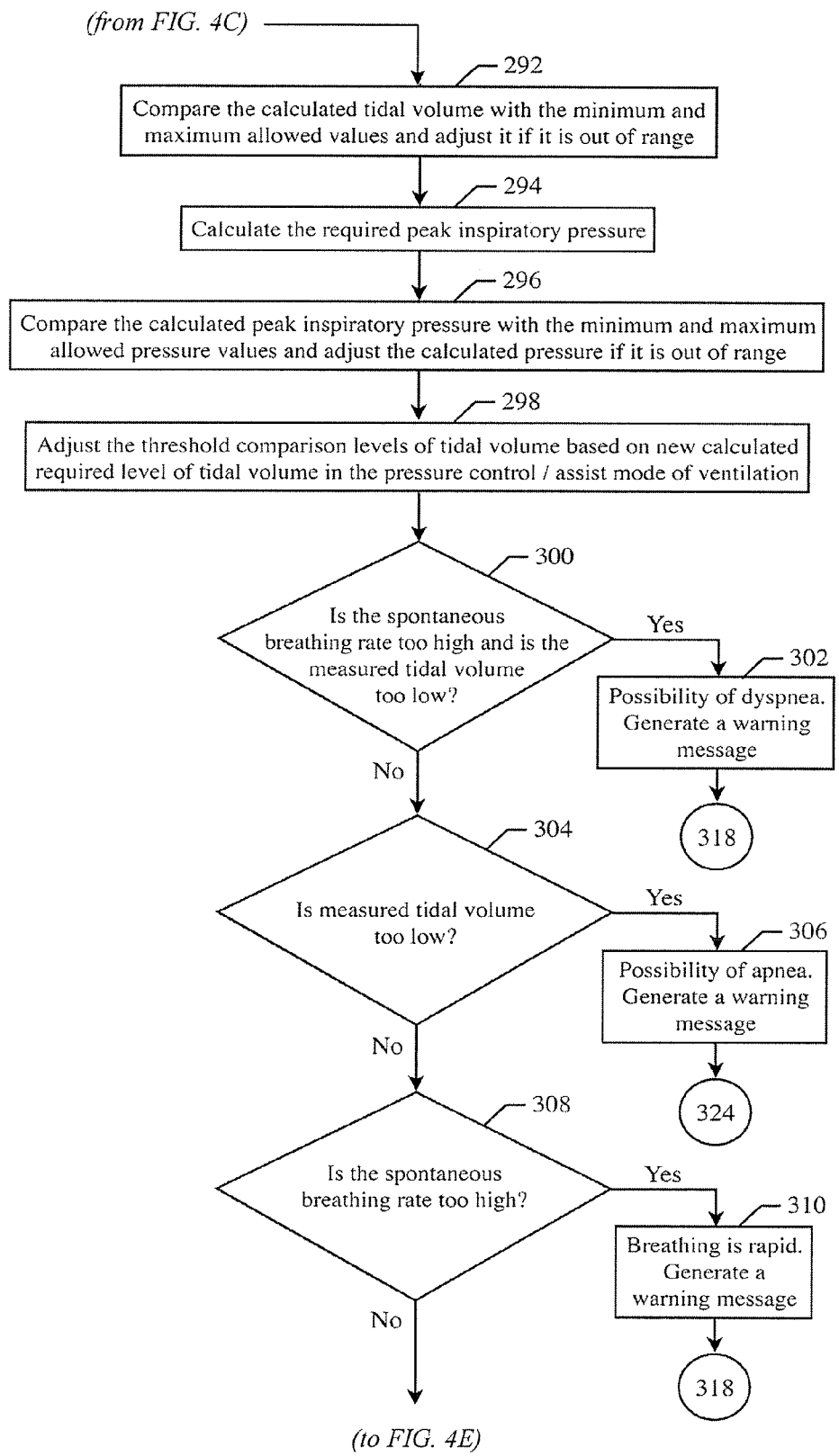
Figure 4E:
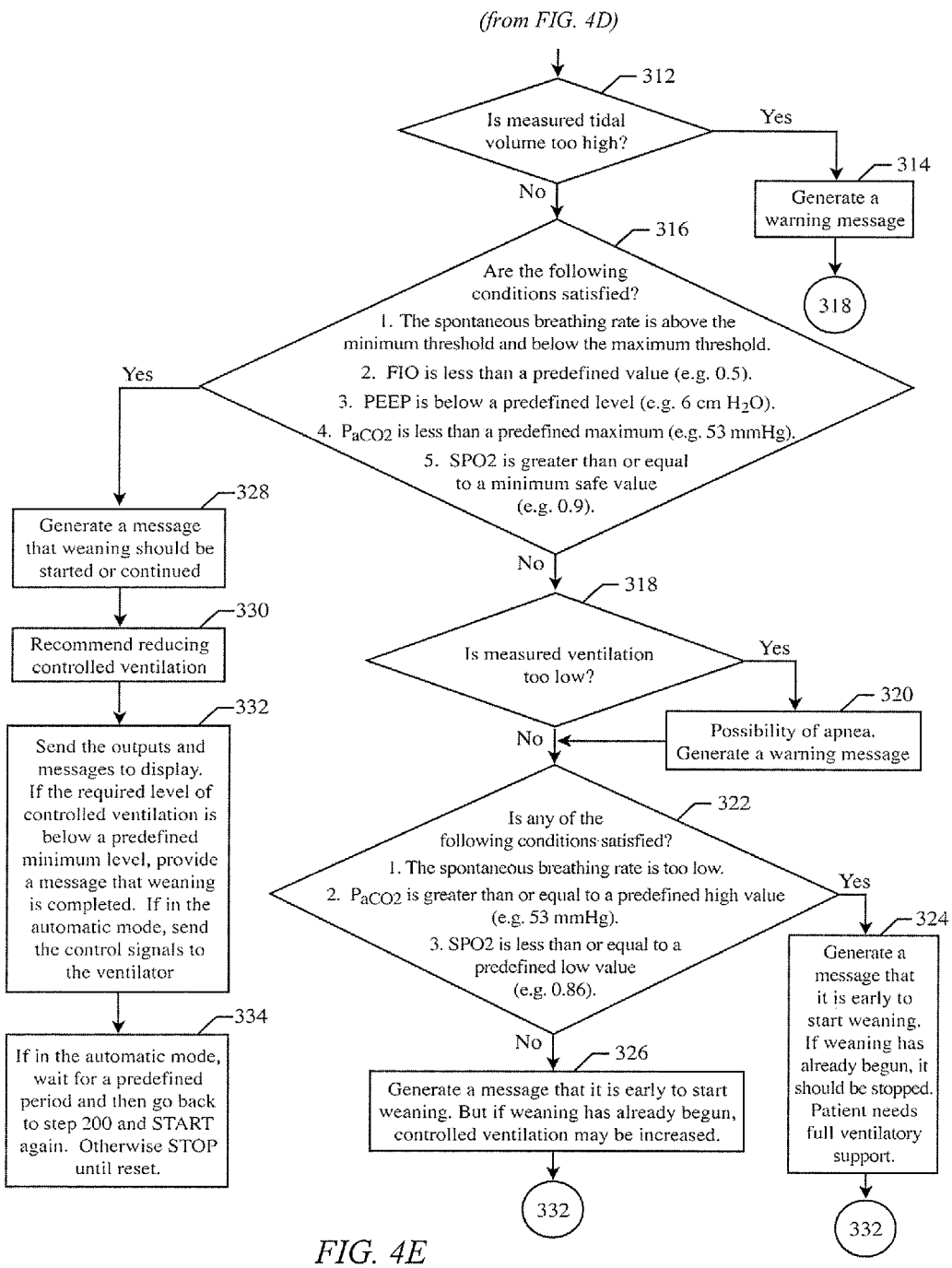

FIG. 3 shows the main options of the software used in a preferred method of the invention. In one embodiment, where computer 12 provides a clinician with a graphical user interface on a display unit, the main options may be displayed as a virtual switchboard, as indicated in the figure. To access these options, a user starts up the software in an initial step 100. At step 100 at the start of the program, the user is provided with four options, any one of which may be directly selected after step 100. From left to right, the first option 110 is a Help & Guidance option, which allows a user to view the software guidelines and get help. The second option 120 is a Create New Patient File option, which allows a user to create a new file for a new patient. The third option 130 is Follow Up on An Existing Patient. This option allows a user to continue use of the software for a patient whose personal history may already be logged in the computer memory or who has had prior respiratory therapy on the system according to the invention. The fourth option 140 is View Patient's Data, which allows a user to view a patient's accumulated data stored in system memory.

In one embodiment, selecting option 120 allows a user to enter patient data such as name, ID number, gender, ideal body weight, etc., and begin respiratory therapy for the patient. For example, in Decision Support mode, the user selecting option 120 may then enter ventilator data by reading data from the mechanical ventilator 10 and entering that data into computer 12 via user interface 13. The user may then wait for computer 12 to output an instruction, responsive to patient and ventilator input data, for display on the display unit. The user may receive the instruction by reading the display unit, and then take appropriate action, for example, by adjusting a control on mechanical ventilator 10, adjusting a sensor connected to the patient, or by taking some action to stop the respiratory therapy. In Open Loop Manual mode, the user selecting option 120 may need only enter patient nominal data such as name, ideal body weight, etc. Computer 12 will then automatically provide decision support to the clinician by displaying instructions for respiratory therapy, and the clinician may then act on the instructions by manually controlling mechanical ventilator 10 in accordance with the instructions. In Closed Loop Automatic mode, the user selecting option 120 may need only enter patient nominal data, then allow computer 12 to automatically administer respiratory therapy to the patient (including weaning the patient) through closed-loop control as described above with reference to FIGS. 1 & 2, and according to automated processes described below in further detail. In this mode, the user may supervise the automatic therapy, and may at any time intervene through user interface 13. For existing patients, a user selecting option 130 need not enter nominal data for the patient, as that data may already be logged in computer memory. After selecting option 130, respiratory therapy or weaning may be administered in any desired mode.

FIGS. 4A-4E show a process flow chart of one embodiment of a preferred sequence of steps executed to carry out a method of the invention. Those skilled in the art will appreciate that the sequence of steps may be easily reduced to source code instructions for input to and execution by a processor or computer using standard programming languages such as Basic, Visual Basic, or other languages. As can be seen after the start of the flow chart at 200, the input data are read at 202. The input data may include patient and ventilator data such as patient's ideal body weight (WEIGHT), body temperature (TEMP), respiratory airway resistance (RES), respiratory compliance (COMP), $CO_2$ level (PCO2), arterial oxygen saturation (SPO2), as well as positive end-expiratory pressure (PEEP), the inspired oxygen fraction (FIO), total respiratory rate (F2), the inspiratory to expiratory time ratio (TI/TE), the spontaneous breathing rate (FSP), the peak inspiratory pressure (SPN), tidal volume (VTS), measured tidal volume (VTMS) which may be spontaneous tidal volume for spontaneously breathing patients, maximum allowed tidal volume (VMAX), and maximum allowed pressure (PMAX). Data indicative of the mode of ventilation (VM) is also provided at this stage (e.g. VM is 1 in the pressure control/assist modes and is zero in the volume control/assist modes).

At step 204 that follows, each data is compared to a predefined acceptance range and if it is not within the specified range, its value is rejected and an error message is generated. In the next step, 206, the maximum allowed respiratory rate can be calculated as:

$$FMM = 60/(5 \times RES \times COMP)$$

where FMM is the maximum allowed respiratory rate in breaths/minute, RES is respiratory airway resistance in cm $H_2O$/liter/second, and COMP is respiratory compliance in liter/cm $H_2O$.

At the next step, 208, the system checks whether patient's PCO2 data is provided. This data can be provided by many different means and methods of measurement known to those skilled in the art. For example, a gas analyzer may be used to measure the end-tidal $CO_2$ pressure. The patient's arterial pressure of $CO_2$ may be obtained as:
ti $P_{aCO2} = PCO2 + K1$
where $P_{aCO2}$ is the partial pressure of $CO_2$ in the patient's arterial blood, PCO2 may be the end-tidal pressure of $CO_2$, and K1 is the difference between $P_{aCO2}$ and PCO2 which can also be used to set a desired $P_{aCO2}$ level for the patient based on his/her conditions. The unit for the variables in this equation can be mmHg.

If PCO2 data is provided, the next step at 218 is followed in which alveolar ventilation is computed. In this computation, if $P_{aCO2}$ is less than a predefined threshold level (e.g. 33 mmHg), then the effect of PCO2 on ventilation is set to zero. Otherwise, the net effect of PCO2 on alveolar ventilation is calculated as:

$$VAC = C1 \times P_{aCO2} - C2$$

where VAC is the ratio of alveolar ventilation as the net effect of $P_{aCO2}$ to the resting value of alveolar ventilation and C1 and C2 are constants (examples of C1 and C2 are 0.405 and 14.878, respectively, where $P_{aCO2}$ is in mmHg). Also at step 218, the net effect of patient's oxygen level on ventilation is computed. There are many techniques known to those skilled in the art to measure a patient's blood oxygen level. If the non-invasive method of pulse oximetry is used for such a measurement, the patient's arterial partial pressure of oxygen, $P_{aO2}$, may be found from arterial oxygen saturation data, SPO2, from the pulse oximeter as:

$$P_{aO2} = \frac{-\ln[1 - (SPO2)^{0.5}]}{0.046} + C3$$

where $P_{aO2}$ is in mmHg and C3 is a constant added to shift and correct $P_{aO2}$ based on the patient's blood pH level. If the patient's blood pH level is in the 7.45-7.55 range, C3 is set to zero. Otherwise C3 is adjusted by /−3.5 mmHg per every −/+0.1 deviation in blood pH from the above range.

At step 218, if $P_{aO2}$ is greater than a predefined value (e.g. 104 mm Hg), then the net effect of oxygen on ventilation is zero. Otherwise:

$$VAO=(4.72\times10^{-9})\times(104-P_{aO2})^{4.9}$$

where VAO is the ratio of alveolar ventilation as the net effect of oxygen to the resting value of alveolar ventilation.

At the end of the calculations in step 218, the total alveolar ventilation is calculated as:

$$VALV=(VAO+VAC)\times VALV(\text{rest})$$

where VALV and VALV(rest) are alveolar ventilation and alveolar ventilation at rest in liters/min respectively. VALV (rest) may be found as:

$$VALV(\text{rest})=(0.056333/66)\times WEIGHT\times 60$$

where WEIGHT is the patient's ideal body weight in Kg. WEIGHT may be input to the system or patient's height may be used to determine WEIGHT. If this input is not provided, a default value may be used. Also, if ventilation at rest is provided as input, it will indicate WEIGHT and works the same way as described above.

At step 220 that follows, the computed alveolar ventilation found at step 218 is compared to a predefined minimum and if it is too low, it's value is increased.

At the next step at 222, the patient's respiratory dead space volume is calculated if not provided. The following empirical equation may be used to calculate the dead space volume:

$$VD=0.1698\times(VALV/60)+0.1587$$

where VD is respiratory dead space volume in liters.

In the next step, 224, the optimum respiratory rate to minimize the respiratory work rate is calculated as:

$$F1 = 60\times\left[\frac{-K'\times VD + \sqrt{(K'\times VD)^2 + 4\times K'\times RES\times\Pi^2\times\left(\frac{VALV}{60}\right)\times VD}}{2\times RES\times\Pi^2\times VD}\right]$$

where F1 is the optimum total respiratory rate in breaths/minute and K' is the respiratory elastance (reciprocal of compliance, 1/COMP). The above equation is a modified version of an equation derived for optimum frequency of breathing by A. B. Otis et al., "Mechanics of Breathing in Man," Journal of Applied Physiology, Vol. 2, pages 592-607, 1950.

In the next step, 226, the computed breathing frequency is compared with a predefined minimum rate and the maximum rate found in step 206, and it is adjusted if found outside the range. Then at step 228 that follows, minute ventilation is calculated as:

$$MV=VALV+F1\times(VD+VED)$$

where VED is the added dead space due to tubes and connections to the ventilator and MV is minute ventilation in liters/minute.

In the next step at 230, the expiratory time is compared to a minimum value and the TI/TE ratio is adjusted if the expiratory time is too short, in order to prevent build up of intrinsic PEEP. The minimum expiratory time may be defined as:

$$TEMIN=2.5\times RES\times COMP$$

where TEMIN is the minimum expiratory time in seconds.

Back to step 208, if patient's PCO2 data is not provided, its value is assumed to be normal (e.g. 39 mmHg), but the program passes to step 210 in which minute ventilation, MV, is calculated by using the patient's ideal body weight and temperature (if temperature input is not provided, a default value such as 37° Celsius may be assumed). The following equations may be used for this calculation:

$$V'=(6.7/66)\times WEIGHT$$

If TEMP>37° Celsius, then MV=V'+0.08×V'×(TEMP−37)

Otherwise if TEMP≤37° Celsius, then MV=V'

In the next step at 212, the patient's respiratory dead space is calculated. This may be done by using the ideal body weight as:

$$VD=0.0026\times WEIGHT$$

In the next step at 214, the optimum respiratory rate is computed for minimum respiratory work rate by using the same equation that was discussed in step 224. In order to solve the equation, VALV will be substituted by (MV−F1×VD) in the equation and since MV and VD have already been found at steps 210 and 212, the equation can be solved for F1 by using an iterative trial and error procedure. Then at the next step, 216, the computed respiratory rate is compared to a predefined minimum rate and the maximum rate found in step 206, and is adjusted if it is out of range. Then control passes to step 230 in which the inspiratory to expiratory time ratio is adjusted if necessary as discussed before.

After step 230, the program passes to step 232 in which the patient's oxygen data that may be the arterial oxygen saturation measured by a pulse oximeter (SPO2) is examined. At step 234 that follows, SPO2 is compared to a high threshold value (e.g. 0.95). If SPO2 is greater than or equal to the high threshold value, at step 236, FIO is compared to a low value (e.g. 0.25). If FIO is found to be higher than 0.25 for example, then its value may be reduced at step 238 as:

New $FIO=0.25+(FIO-0.25)\times 0.65$ and then control passes to step 276 which will be described later. Otherwise, if at step 236, FIO is not found to be higher than 0.25, its value is not changed at step 240, and then control passes to step 276.

Back to step 234, if SPO2 is less than the high threshold value (e.g. 0.95), the next step at 242 is performed in which SPO2 is compared to a second threshold value (e.g. 0.94). If SPO2 is greater than or equal to the second threshold value, the next step at 244 is performed in which FIO is compared to another relatively low level (e.g. 0.3). For example, if it is greater than 0.3, then its value may be reduced at step 246 by:

New $FIO=0.3+(FIO-0.3)\times 0.65$ and then control passes to step 276. Otherwise, if at step 244, FIO is not found to be greater than 0.3, its value is not changed in step 248, and then program passes to step 276.

Back to step 242, if SPO2 is less than the second threshold value (e.g. 0.94), then it is compared to a third threshold value (e.g. 0.92) at step 250. If SPO2 is greater than or equal to the third threshold value, then at the next step at 252, FIO is compared to a predefined value (e.g. 0.4). For example, if FIO is less than 0.4, then it is raised to 0.4 at step 254 and program passes to step 276. But if at step 252, FIO is found to be greater than or equal to 0.4, its value is not changed in step 256, and control is transferred to step 276.

Back to step 250, if SPO2 is less than the third threshold value (e.g. 0.92), then at the next step, 258, it is compared to a fourth threshold value (e.g. 0.91). If SPO2 is found to be greater than or equal to the fourth threshold value, at the next step at 260, FIO is compared to another predefined value (e.g. 0.45). If FIO for example is less than 0.45, then its value is raised to 0.45 at step 264 and program passes to step 276. Otherwise FIO is not changed at step 262 and control transfers to step 276.

Back to step 258, if SPO2 is less than the fourth threshold value (e.g. 0.91), then at the next step at 265 a warning message is generated and in the step that follows at 266, FIO is compared to a predefined high value that can be up to 1. In the flow chart a conservative value of 0.65 is used for this high FIO value as an example. If FIO is less than this high value, it is raised to that level at step 268 and then step 270 is performed in which PEEP is increased by a predefined increment (e.g. 2 cm $H_2O$), and control passes to step 276. But if at step 266, FIO is not found to be less than the predefined high level, its value is not changed in step 272 that follows and at the next step, 274, PEEP is increased by a predefined increment (e.g. 2 cm $H_2O$), and then control passes to step 276.

At the next step, 276, the "RATIO" of PEEP to FIO is calculated as follows:

$$RATIO = PEEP/(FIO \times 100).$$

This RATIO is compared to a predefined minimum (e.g. 0.12) at step 278. If it is less than the minimum value, PEEP is raised at step 280 and control passes to step 286. If at step 278, RATIO is not found to be low, then at step 282 that follows, it is compared to a predefined maximum value (e.g. 0.24). If RATIO is greater than the maximum value, PEEP is reduced at step 284 and then control transfers to step 286. However, if at step 282, RATIO is not found to be too high either, then no adjustment is done to PEEP and control transfers to step 286. It should be noted that between two successive increases in PEEP, it is preferred that a certain time gap is allowed so that the PEEP change affects the oxygenation status of the patient. Therefore, at steps 270, 274, and 280, PEEP is increased only if adequate time has passed since the last change in PEEP was made, and the time gap may be specified by the clinician. Imposition of the time gap between two successive increases in PEEP is particularly important if the invention is used to automatically control the ventilator.

At step 286 that follows next, minimum and maximum comparison levels for respiratory rate and tidal volume are defined. These levels will be used to determine the status of the patient, and whether the patient should be considered for weaning or not. As examples, these levels may be defined as:

$$F1N = 0.45 \times F1$$

$$F2M = 1.8 \times F1$$

$$VTM = 0.7 \times \text{tidal volume}$$

$$VTL = 1.6 \times \text{tidal volume}.$$

In the above equations, F1N and VTM are minimum comparison levels for respiratory rate and tidal volume, and F2M and VTL are maximum comparison levels for respiratory rate and tidal volume respectively. It should be noted that "tidal volume" used in the above equations may be the data provided by the ventilator as the set tidal volume on the ventilator (VTS), or maybe adjusted later based on the new calculated value of optimal tidal volume. Also, in ventilation assist modes that all breaths are triggered by the patient such as pressure support mode, F1N may need to be defined at a higher level such as 0.75×F1.

In the next step at 288, the required tidal volume is calculated as:

$$\text{tidal volume} = MV/F1$$

In the next step, 290, the minimum allowed tidal volume and a comparison level for minute ventilation maybe defined as:

$$VTMIN = 2 \times VD + VED$$

$$VREQ = 0.85 \times MV$$

In the above example equations, VTMIN is the minimum allowed tidal volume, and VREQ is a comparison value for minute ventilation.

In the next step, 292, the calculated tidal volume in step 288 is compared to VTMIN and VMAX, and if it is outside this range, its value is adjusted. In the step that follows at 294, the total required peak inspiratory pressure in the pressure control/assist modes is calculated as:

$$\text{Peak Inspiratory Pressure} = [\text{tidal volume}/COMP] + PEEP$$

Then control passes to step 296 in which the calculated peak inspiratory pressure is compared to a maximum allowed pressure which may be defined as (PMAX−8 cm $H_2O$) and a minimum level that may be defined as PMIN=PEEP+5 cm $H_2O$. If the peak inspiratory pressure is not within this range, its value is adjusted at step 296.

At the next step at 298, the comparison levels for tidal volume, VTM and VTL, which were defined in step 286, are redefined preferably in the pressure control/assist modes of the ventilator based on the new calculated value of the tidal volume by using the following example equations:

$$VTM = 0.7 \times \text{tidal volume}$$

$$VTL = 1.6 \times \text{tidal volume}$$

At the step 300 that follows next, the spontaneous breathing rate, FSP, and the measured tidal volume, VTMS, are simultaneously examined. If FSP is higher than or equal to F2M and VTMS is lower than VTM, then the possibility of dyspnea is detected and a warning message is generated at step 302 and control passes to step 318 which will be described later. However, if at step 300, FSP is not found to be too high with VTMS being too low, the next step at 304 is performed. At this step, measured tidal volume, VTMS, is compared to VTM. If VTMS is less than VTM, at step 306, the possibility of apnea is detected, a warning message is generated, and then control passes to step 324 which will be described later.

However, if at step 304, VTMS is not found to be less than VTM, the next step at 308 is performed in which FSP is compared to F2M. If FSP is higher than or equal to F2M, then rapid breathing is detected at step 310, a warning message is generated, and control passes to step 318. However, if at step 308, FSP is not found to be too high, the next step at 312 is performed in which measured tidal volume, VTMS, is compared to VTL. If VTMS is higher than or equal to VTL, a warning message is generated at the next step, 314, and program transfers to step 318. If at step 312, VTMS is found to be less than VTL, then step 316 is performed in which multiple conditions are checked. Those conditions may be the following:

Is FSP greater than F1N and less than F2M?
Is FIO less than a predefined value (e.g. 0.5)?
Is PEEP less than a predefined level (e.g. 6 cm $H_2O$)?
Is $P_{aCO2}$ less than a predefined value (e.g. 53 mmHg)? Is SPO2 greater than or equal to a minimum safe value (e.g. 0.9)?

If the answers to all or selected ones among the above questions are yes at step 316 (for example for more stable patients, it may be sufficient that only the first condition be checked) then at step 328 that follows, weaning is recommended to be started, or continued if started already, and a message is generated to convey the recommendation to the clinician. Next, at step 330, recommendation is made to reduce controlled level of ventilation by a certain predefined percentage (e.g. 15% to 20%), and control passes to step 332. Reduction of the controlled level of ventilation may be done in different ways. For example, the minute ventilation supplied by the ventilator may be reduced as compared to the optimal required minute ventilation calculated by the program by a prescribed percentage. Or, as another example, in the pressure support mode, the level of pressure support supplied by the ventilator may be reduced by a certain percentage (e.g. 15% to 20%) as compared to the required peak inspiratory pressure computed by the program.

At step 332, the optimal ventilatory parameters for the patient and the messages generated by the system are sent to display. If the invention is used to control the mechanical ventilator automatically, the required outputs are sent to the ventilator to control its outputs at this step. It should be noted that in the automatic weaning mode, while the output signal to the ventilator for controlling the level of ventilation such as pressure support is reduced periodically, but the control signals for FIO and PEEP are adjusted only according to the calculated required values of these outputs and are not subjected to any reduction due to weaning.

In the next step at 334, the system is instructed to wait for a predetermined period of time if it is used to control the mechanical ventilator automatically, and after the wait time is over, control passes to step 200 at the start of the program and continues again. Otherwise, if the invention is not used to control the ventilator automatically, it stops at step 334 until it is restarted by the human operator.

Back to step 316, if the necessary conditions for weaning are not satisfied, then the next step at 318 is performed. At step 318, measured minute ventilation is compared to a minimum required level, VREQ, which was defined in step 290. If measured ventilation is lower than VREQ, possibility of apnea is detected at step 320, a warning message is generated, and control passes to step 322. But if at step 318, measured ventilation is not found to be low, then step 320 is not performed and control is transferred to step 322.

At step 322, the following conditions are checked:
Is $P_{aCO2}$ greater than or equal to a predefined high value (e.g. 53 mmHg)?
Is SPO2 less than or equal to a predefined low value (e.g. 0.86)?
Is the spontaneous breathing rate too low (e.g. below F1N)?

If the answer to any of the above questions at step 322 is yes, then at the next step at 324, a message is generated that it is too early to start weaning, and if already started, weaning should be stopped and the patient should be switched back to full ventilatory support (e.g. assist control), and program transfers to step 332. However, if at step 322, the answers to all questions are no, then control passes to step 326 in which a message is generated that weaning should not be started, but if it has already begun, it may continue with increased controlled ventilation (e.g. raised to the previous higher level), and then program passes to step 332 (if the amount of ventilation checked at step 318 was not low, controlled ventilation may not need to be increased at step 326 if measured tidal volume is higher than the acceptable range).

In the automatic mode if breaths are patient triggered, in addition to the above-described procedure, the system also watches for prolonged apnea, and if no breath is triggered by the patient for a predefined period of time (e.g. 25 seconds), it automatically switches back to mandatory breathing with full ventilatory support.

It should be noted, that many of the constant parameters in the equations described above were examples for use in the treatment of adult patients which may be modified for different patients. Also, if the invention is used for pediatric or neonatal treatments, many of the constant parameters will need to be changed.

Figure 5:
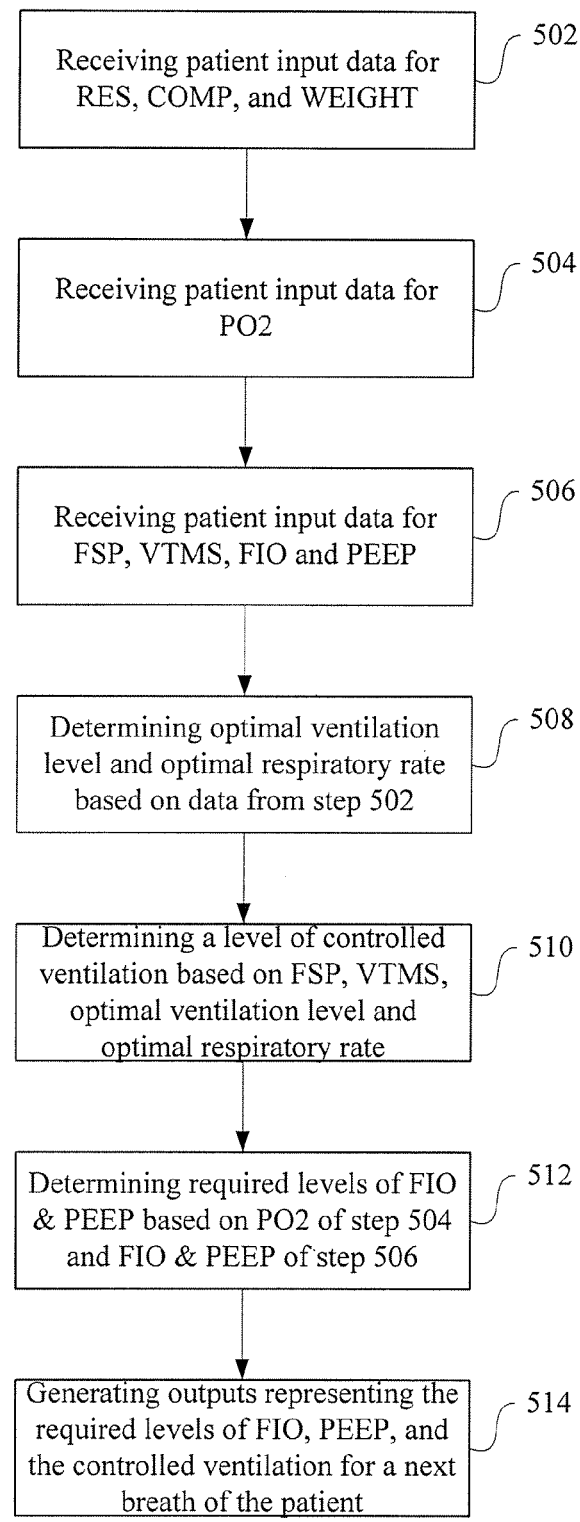
FIG. 5 is a process flow diagram of a method for optimizing mechanical ventilation of a patient according to the invention.

With the foregoing apparatus and processes in mind, various other embodiments of methods are possible within the scope of the invention. One such embodiment is a method 500 illustrated in the process flow diagram of FIG. 5. This is a general application method for optimizing mechanical ventilation of a patient. The method begins at step 502, in which patient input data representing RES, COMP and WEIGHT is received, for example, at the input terminals of a processor such as computer 12. In the next step 504, input data representing patient oxygen level PO2 is received, for example, from a pulse oximeter or other transducing source. In the next step 506, additional input data is received. This input data may include FSP, VTMS, FIO, and PEEP, and may be received directly from a mechanical ventilator such as ventilator 10.

The next three steps are computational steps, preferably performed automatically by a digital processor executing algorithms according to the invention. In step 508, optimal ventilation level and optimal respiratory rate are determined based on all or a portion of the patient input data (RES, COMP, and WEIGHT) that was received in step 502. In the next step 510, a level of controlled ventilation is determined for the patient based on FSP, VTMS, the optimal ventilation level, and the optimal respiratory rate. In the third computational step 512, the method determines required levels of FIO and PEEP based on PO2 data received in step 504 and on FIO and PEEP data received in step 506. In the final step 514, one or more output signals are generated. These outputs may represent the required levels of FIO, PEEP, ventilation, respiratory rate, or the controlled ventilation needed for a next breath of the patient.

Figure 6:
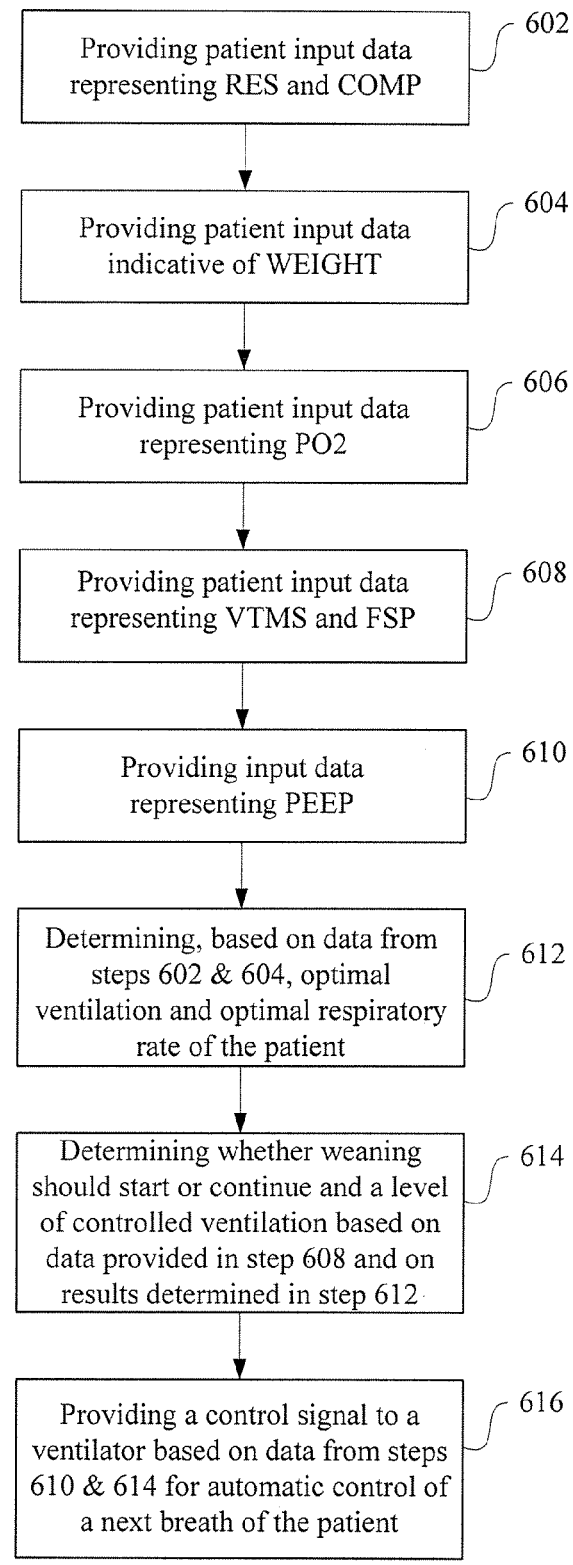
FIG. 6 is a process flow diagram of a method for automatically weaning a patient from mechanical ventilation according to the invention.

FIG. 6 illustrates another generalized method according to the invention. This method 600 may be practiced to determine whether weaning is appropriate for a patient, and if so, to provide a controlled way to safely wean the patient from reliance on a mechanical ventilator.

Method 600 begins at step 602, which includes providing patient input data representing RES and COMP. This data is provided, for example, to a computing system executing the control algorithms of the present invention. At the next step 604, additional patient input data indicative of the patient's WEIGHT is provided. This data may be patient's ideal body weight, height, ventilation level at rest, or any other data that may be used as indicative of patient's ideal body weight by those skilled in the art. In the next step 606, data for the patient's oxygen level is provided. In the next step 608 patient input data representing VTMS and FSP is provided, and in step 610, patient input data representing PEEP is provided. Patient data provided in steps 602-610 may originate from one or more individual transducers connected to the patient, from direct outputs received from a mechanical ventilator, or from a control circuit that derives the patient data from transducers, ventilator outputs, or user inputs (the data indicative of WEIGHT is preferably stored in software).

A calculation step 612 is next in the process sequence. In step 612, an optimal ventilation and an optimal respiratory rate are determined for the patient, based on data provided in steps 602 & 604. Next, in step 614, a decision is made whether to start weaning, or whether to continue weaning, if weaning has already started. If weaning is to start or continue, step 614 also determines a controlled ventilation level based on data provided in step 608 and also on results determined in step 612. Finally, in step 616, a control signal is provided to the ventilator to automatically control a next breath of the patient. The control signal may be based on data from step 614.

There has been described a method and apparatus that can be used for automatic respiratory control and weaning of patients on mechanical ventilation as well as a decision support system in the treatment of such patients. Those skilled in the art appreciate modifications to the specific parameters described herein that can be made without departing from the spirit of the invention, and such modifications are included in the invention. This invention can be embodied in other specific forms without departing from the spirit or essential attributes thereof, and accordingly, the invention is not limited to the foregoing preferred embodiments and reference should be made to the appended claims rather than to the foregoing specification as indicating the scope of the invention.

What is claimed is:

1. A method encoded on a data storage medium as executable software for optimizing mechanical ventilation of a patient, the method comprising steps of:
   (a) receiving patient input data representing respiratory airway resistance (RES), respiratory compliance (COMP), and data indicative of patient's ideal body weight (WEIGHT);
   (b) receiving data representing patient oxygen level (PO2);
   (c) receiving input data representing measured spontaneous breathing rate (FSP), tidal volume (VTMS), inspired oxygen fraction (FIO), and positive end-expiratory pressure (PEEP);
   (d) determining optimal ventilation level and optimal respiratory rate for the patient based on data received in step (a);
   (e) determining a level of controlled ventilation for the patient based on the FSP, the VTMS, the optimal ventilation level, and the optimal respiratory rate;
   (f) determining required levels of FIO and PEEP based on the patient oxygen level data received in step (b) and the patient FIO and PEEP data received in step (c); and
   (g) generating outputs representing the required levels of FIO, PEEP, and the controlled ventilation for a next breath of the patient;
   the steps performed by a processor executing the software.

2. The method of claim 1 wherein step (e) further comprises determining whether to start or continue weaning the patient based on the FSP, the VTMS, the optimal ventilation level, and the optimal respiratory rate, and if so, determining the level of controlled ventilation for optimal weaning.

3. The method of claim 2 further comprising
   comparing FSP to an FSP acceptance range based on the determined optimal respiratory rate;
   comparing VTMS to a VTMS acceptance range; and
   if FSP and VTMS are both within their respective acceptance ranges, determining that weaning should start or continue with a lowered level of controlled ventilation.

4. The method of claim 2 further comprising
   comparing FSP to an FSP acceptance range based on the determined optimal respiratory rate;
   comparing VTMS to a VTMS acceptance range; and
   if FSP exceeds a maximum of the FSP acceptance range, if VTMS is less than a maximum of the VTMS acceptance range, and if PO2 exceeds a predefined value, determining that weaning should continue with an increased level of controlled ventilation.

5. The method of claim 2 further comprising
   comparing FSP to an FSP acceptance range based on the determined optimal respiratory rate;
   comparing VTMS to a VTMS acceptance range; and
   determining that weaning should continue if the FSP is higher than or equal to a minimum value of the FSP acceptance range, if PO2 exceeds a predefined value, and if VTMS exceeds a maximum of the VTMS acceptance range.

6. The method of claim 2 wherein step (b) further comprises receiving data representing patient carbon dioxide level (PCO2);
   wherein step (d) further comprises determining optimal ventilation level and optimal respiratory rate for the patient based on data received in step (a) and step (b); and
   further comprising comparing FSP to an FSP acceptance range based on the determined optimal respiratory rate;
   comparing VTMS to a VTMS acceptance range; and
   determining that weaning should start, or should continue with lowered level of controlled ventilation if started already, if FSP and VTMS are both within their respective acceptance ranges.

7. The method of claim 2 wherein step (b) further comprises receiving data representing patient carbon dioxide level (PCO2);
   wherein step (d) further comprises determining optimal ventilation level and optimal respiratory rate for the patient based on data received in step (a) and step (b); and
   further comprising comparing FSP to an FSP acceptance range based on the determined optimal respiratory rate;
   comparing VTMS to a VTMS acceptance range; and
   determining that weaning should continue if FSP is higher than or equal to a minimum value in the FSP acceptance range, if PO2 is above a predefined value, if PCO2 is below a predefined value, and if VTMS exceeds a maximum of the VTMS acceptance range.

8. The method of claim 2 wherein step (b) further comprises receiving data representing patient carbon dioxide level (PCO2);
   wherein step (d) further comprises determining optimal ventilation level and optimal respiratory rate for the patient based on data received in step (a) and step (b); and
   further comprising comparing FSP to an FSP acceptance range based on the determined optimal respiratory rate;
   comparing VTMS to a VTMS acceptance range; and
   determining that weaning should continue with increased level of controlled ventilation if VTMS is below a maximum of the VTMS acceptance range, if PO2 exceeds a predefined value, if PCO2 is below a predefined value, and if the FSP exceeds a maximum of the FSP acceptance range.

9. The method of claim 2 wherein step (b) further comprises receiving data representing patient carbon dioxide level (PCO2);
   wherein step (d) further comprises determining optimal ventilation level and optimal respiratory rate for the patient based on data received in step (a) and step (b); and
   further comprising comparing FSP to an FSP acceptance range based on the determined optimal respiratory rate;
   comparing VTMS to a VTMS acceptance range; and determining that weaning should start, or should continue with a lowered level of controlled ventilation if started already, if FSP and VTMS are both within their respective acceptance ranges, if PO2 exceeds a predefined value, and if PCO2 is below a predefined level.

10. The method of claim 9 further comprising determining that weaning should start, or should continue with a lowered level of controlled ventilation if already started, if required FIO is below a predefined value and if required PEEP is also below a predefined value.

11. The method of claim 2 wherein the outputs generated in step (g) are signals that are supplied to a mechanical ventilator to control it automatically.

12. The method of claim 1 wherein the optimal respiratory rate is computed to minimize respiratory work rate.

13. The method of claim 12 wherein data received in step (a) includes data representing patient body temperature (TEMP).

14. The method of claim 13 wherein data representing inspiratory to expiratory time ratio (TI/TE) is provided in step (c).

15. The method of claim 14 further comprising adjusting the TI/TE ratio so that expiration time TE=0.5/fmax, where fmax is a maximum allowed respiratory rate calculated as:

$$fmax=1/(5 \times RES \times COMP).$$

16. The method of claim 13 wherein the optimal ventilation level, MV, in liters/minute is calculated as:

$$MV=V'+\alpha \times V' \times (TEMP-37) \text{ for TEMP} \geq 37,$$

$$MV=V' \text{ for TEMP}<37,$$

where $V'=\beta \times WEIGHT$, WEIGHT is in Kg, TEMP is in degrees C., and $\alpha$ and $\beta$ are constants.

17. The method of claim 16 wherein the optimal respiratory rate is calculated as:

$$F1 = 60 \times \left[ \frac{-K' \times VD + \sqrt{(K' \times VD)^2 + 4 \times K' \times RES \times \Pi^2 \times \left(\frac{VALV}{60}\right) \times VD}}{2 \times RES \times \Pi^2 \times VD} \right]$$

where F1 is the optimal respiratory rate in breaths/minute, K' is respiratory elastance (reciprocal of COMP) in cmH$_2$O/liter, RES is in cmH$_2$O/liter/second, VD is respiratory dead space in liters, and VALV=MV−F1×VD.

18. The method of claim 17 wherein VD is received as patient input data.

19. The method of claim 17 wherein VD is calculated as: VD=0.0026×WEIGHT.

20. The method of claim 1 wherein step (b) further comprises receiving data representing patient carbon dioxide level (PCO2) and wherein step (d) further comprises determining optimal ventilation level and optimal respiratory rate for the patient based on data received in step (a) and step (b).

21. The method of claim 20 wherein the optimal respiratory rate is computed to minimize respiratory work rate.

22. The method of claim 21 wherein the optimal ventilation comprises optimal alveolar ventilation, VALV, which is calculated as:

$$VALV=(VAO+VAC) \times VALV(rest)$$

where VAO=$4.72 \times 10^{-9} \times (104-PaO2)^{4.9}$ for PaO2<104 mm Hg, and VAO=0 for PaO2≥104 mm Hg, and VAC=C1× PaCO2−C2 for PaCO2 greater than a predefined value and VAC=0 otherwise, and VALV(rest)=K×WEIGHT, where VALV and VALV(rest) are alveolar ventilation and alveolar ventilation at rest in liters/minute respectively, PaO2 and PaCO2 are partial pressures of oxygen and carbon dioxide in patient's arterial blood in mmHg respectively, and C1, C2, and K are constants.

23. The method of claim 22 wherein PaCO2 is obtained from: PaCO2=PCO2+K1,
where PCO2 is patient's end-tidal pressure of carbon dioxide and K1 is a constant.

24. A method in accordance with claim 22 wherein PaO2 is obtained as:

$$P_{aO2} = \frac{-\ln[1 - (SPO2)^{0.5}]}{0.046} + C3$$

where SPO2 is patient's arterial oxygen saturation measured by pulse oximetry and C3 is a shifting constant that depends on patient blood pH level.

25. A method in accordance with claim 22 wherein the optimal respiratory rate is calculated as:

$$F1 = 60 \times \left[ \frac{-K' \times VD + \sqrt{(K' \times VD)^2 + 4 \times K' \times RES \times \Pi^2 \times \left(\frac{VALV}{60}\right) \times VD}}{2 \times RES \times \Pi^2 \times VD} \right]$$

where F1 is the optimal respiratory rate in breaths/minute, K' is respiratory elastance (reciprocal of COMP) in cmH$_2$O/liter, RES is in cmH$_2$O/liter/second, VD is respiratory dead space in liters, and VALV=MV−F1×VD.

26. The method of claim 25 wherein VD is received as patient input data.

27. The method of claim 25 wherein VD is calculated as:

$$VD=0.1698 \times (VALV/60)+0.1587.$$

28. The method of claim 1 wherein PO2 is set equal to measured arterial oxygen saturation of the patient (SPO2), and wherein FIO is computed by using a sequential procedure, with SPO2 compared to predefined threshold levels successively and FIO adjusted accordingly.

29. The method of claim 28 wherein the sequential procedure comprises the following steps:
comparing SPO2 with a high threshold value;
if SPO2 is higher than or equal to the high threshold value, reducing FIO down to a predefined low value FR1 but not lower than FR1 as:
new FIO=FR1+(FIO−FR1)×K"
where K" is a factor less than 1;
if SPO2 is lower than the high threshold value, comparing SPO2 with a lower second threshold value, and if it is higher than or equal to the lower second threshold value, reducing FIO down to a predefined value FR2 but not lower than FR2 as:
new FIO=FR2+(FIO−FR2)×K";
if SPO2 is lower than the second threshold value, comparing it with a lower third threshold value, and if SPO2 is higher than or equal to the third threshold value, raising FIO to a predefined value FR3 if it is lower than FR3;
if SPO2 is lower than the third threshold value, comparing it with a lower fourth threshold value, and if it is higher than or equal to the fourth threshold value, raising FIO to a predefined value FR4 if it is lower than FR4; and if SPO2 is lower than the fourth threshold value, comparing FIO with a predefined high value, and if it is lower than the predefined high value, raising FIO to the predefined high value.

30. The method of claim 29 wherein PEEP is increased incrementally if SPO2 is found to be lower than the fourth threshold value and if a predefined minimum time has elapsed since a most recent adjustment in PEEP.

31. The method of claim 30, further comprising
determining a ratio of PEEP to FIO (RATIO);
comparing RATIO to predefined minimum and maximum values for the ratio;
increasing PEEP if RATIO is lower than the minimum value and a predefined minimum time has elapsed since a most recent adjustment in PEEP; and
decreasing PEEP if RATIO exceeds the maximum value to bring RATIO lower than or equal to the maximum value.

32. The method of claim 1 implemented on a digital computer wherein one or more of the data in steps (a) through (c) is provided manually to the computer through a user interface.

33. The method of claim 32 comprising an advisory decision support system, wherein the generated outputs in step (g) cause instructions for a user.

34. The method of claim 1 implemented on a digital processor wherein the input data is provided to the processor automatically.

35. The method of claim 1 wherein the outputs generated in step (g) are signals that are supplied to a mechanical ventilator to control it automatically.

36. An apparatus for optimizing mechanical ventilation of a patient, comprising:
a computing system;
digital readable memory coupled to the computing system; and
transducers providing patient input signals to the computing system representing respiratory airway resistance (RES), respiratory compliance (COMP), and ventilation data representing patient's spontaneous breathing rate (FSP), and measured tidal volume (VTMS);
wherein the computing system executing a program stored in the memory determines output data representing optimal ventilation level and optimal respiratory rate of the patient based on data indicative of patient's ideal body weight (WEIGHT) stored in memory and data representing RES and COMP, and provides output data representing optimal ventilation and optimal respiratory rate and a controlled level of mechanical ventilation based on the optimal ventilation data, the optimal respiratory rate data, FSP, and VTMS.

37. The apparatus of claim 36 further comprising a display unit coupled to the computing system for displaying the output data representing at least one of optimal ventilation level and optimal respiratory rate.

38. The apparatus of claim 36 further comprising a transducer providing input signal representing patient's measured oxygen level (PO2) to the computing system.

39. The apparatus of claim 38 wherein the transducers include a pulse oximeter providing the PO2 input signal and one or more sensors providing the RES and COMP signals.

40. The apparatus of claim 39 further comprising a transducer providing input signal representing measured carbon dioxide level (PCO2) of the patient and wherein the computing system executing the program further determines, based on PO2 and PCO2, required levels of ventilation and respiratory rate of the patient.

41. The apparatus of claim 40 wherein the transducers include an end-tidal carbon dioxide analyzer for providing the PCO2 patient input signal.

42. The apparatus of claim 41 further comprising one or more A/D converters connected between the transducers and the computing system for converting analog signals from the transducers into digital form.

43. The apparatus of claim 38 wherein the transducers further provide to the computing system patient input signals representing positive end-expiratory pressure (PEEP) and inspired oxygen fraction (FIO) and wherein the computing system executing the program determines output data representing required PEEP and required FIO and supplies the required PEEP and the required FIO to the mechanical ventilator.

44. The apparatus of claim 36 further comprising a mechanical ventilator, wherein the determined output data representing either optimal ventilation level and optimal respiratory rate of the patient or a controlled level of mechanical ventilation is supplied to the mechanical ventilator to control it automatically.

45. The apparatus of claim 44 further comprising one or more D/A converters for converting digital output signals from the computing system to analog signals and supplying the analog signals to the mechanical ventilator.

46. A method for automatically controlling a mechanical ventilator to wean a patient from mechanical ventilation, comprising the steps of:
(a) providing patient data representing respiratory airway resistance (RES) and respiratory compliance (COMP);
(b) providing patient data indicative of ideal body weight (WEIGHT);
(c) providing patient data representing measured oxygen level (PO2);
(d) providing patient data representing tidal volume (VTMS) and spontaneous breathing rate (FSP);
(e) providing patient data representing positive end-expiratory pressure (PEEP);
(f) determining based on data provided in steps (a) and (b), optimal ventilation and optimal respiratory rate of the patient;
(g) determining whether weaning should start or continue and a level of controlled mechanical ventilation based on the optimal ventilation, the optimal respiratory rate, and patient data provided in step (d); and
(h) providing a control signal representing a controlled ventilation level based on data from step (g) and supplying the control signal to the mechanical ventilator to control it automatically for a next breath of the patient.

47. The method of claim 46 wherein data received in step (b) includes data representing patient body temperature (TEMP).

48. The method of claim 47 wherein the optimal ventilation, MV, in liters/minute is calculated in step (f) as:

$$MV = V' + \alpha \times V' \times (TEMP - 37) \text{ for } TEMP \geq 37,$$

$$MV = V' \text{ for } TEMP < 37,$$

where $V' = \beta \times WEIGHT$, WEIGHT is in Kg, TEMP is in degrees C, and $\alpha$ and $\beta$ are constants.

49. The method of claim 48 wherein the optimal respiratory rate is calculated as:

$$F1 = 60 \times \left[ \frac{-K' \times VD + \sqrt{(K' \times VD)^2 + 4 \times K' \times RES \times \Pi^2 \times \left(\frac{VALV}{60}\right) \times VD}}{2 \times RES \times \Pi^2 \times VD} \right]$$

where F1 is the optimal respiratory rate in breaths/minute, K' is respiratory elastance (reciprocal of COMP) in cmH$_2$O/liter, RES is in cmH$_2$O/liter/second, VD is respiratory dead space in liters, and VALV=MV−F1×VD.

50. The method of claim 49 wherein VD is provided as patient data.

51. The method of claim 49 wherein VD is calculated as: VD=0.0026×WEIGHT.

52. The method of claim 46 wherein step (c) further comprises providing data representing patient carbon dioxide level (PCO2) and wherein data provided in steps (a), (b), and (c) are used in step (f) to determine the optimal ventilation and the optimal respiratory rate of the patient.

53. The method of claim 52 further comprising providing patient input data representing inspired fraction of oxygen (FIO), and wherein the FIO data, data in step (c), and data representing PEEP are also used in step (g) to determine whether weaning should begin.

54. The method of claim 53 further comprising
comparing FSP to an FSP acceptance range based on the determined optimal respiratory rate;
comparing VTMS to a VTMS acceptance range; and
determining that weaning should start, or should continue with a lowered level of controlled ventilation if started already, if FSP and VTMS are both within their respective acceptance ranges, if PO2 exceeds a predefined value, if PCO2 is below a predefined value, if FIO is lower than a predefined value, and if PEEP is lower than a predefined value.

55. The method of claim 52 wherein the optimal ventilation comprises optimal alveolar ventilation, VALV, which is calculated as:

$$VALV = (VAO + VAC) \times VALV(\text{rest})$$

where VAO=4.72×10$^{-9}$×(104−PaO2)$^{4.9}$ for PaO2<104 mm Hg, and VAO=0 for PaO2≥104 mm Hg, VAC=C1×PaCO2−C2 for PaCO2 greater than a predefined value and VAC=0 otherwise, and VALV(rest)=K×WEIGHT, where VALV and VALV(rest) are alveolar ventilation and alveolar ventilation at rest in liters/minute respectively, PaO2 and PaCO2 are partial pressures of oxygen and carbon dioxide in patient's arterial blood in mm hg respectively, and C1, C2, and K are constants.

56. The method of claim 55 wherein PaCO2 is obtained from: PaCO2=PCO2+K1, where PCO2 is patient's end-tidal pressure of carbon dioxide and K1 is a constant.

57. A method in accordance with claim 55 wherein PaO2 is obtained as:

$$P_{aO2} = \frac{-\ln[1 - (SPO2)^{0.5}]}{0.046} + C3$$

where SPO2 is patient's arterial oxygen saturation measured by pulse oximetry and C3 is a shifting constant that depends on patient blood pH level.

58. A method in accordance with claim 55 wherein the optimal respiratory rate is calculated as:

$$F1 = 60 \times \left[ \frac{-K' \times VD + \sqrt{(K' \times VD)^2 + 4 \times K' \times RES \times \Pi^2 \times \left(\frac{VALV}{60}\right) \times VD}}{2 \times RES \times \Pi^2 \times VD} \right]$$

where F1 is the optimal respiratory rate in breaths/minute, K' is respiratory elastance (reciprocal of COMP) in cmH$_2$O/liter, RES is in cmH$_2$O/liter/second, VD is respiratory dead space in liters, and VALV=MV−F1×VD.

59. The method of claim 58 wherein VD is provided as patient data.

60. The method of claim 58 wherein VD is calculated as:

$$VD = 0.1698 \times (VALV/60) + 0.1587.$$

61. The method of claim 52 further comprising
comparing FSP to an FSP acceptance range based on the determined optimal respiratory rate;
comparing VTMS to a VTMS acceptance range; and
determining that weaning should start, or should continue with lowered level of controlled ventilation if started already, if FSP and VTMS are both within their respective acceptance ranges.

62. The method of claim 52 further comprising
comparing FSP to an FSP acceptance range based on the determined optimal respiratory rate;
comparing VTMS to a VTMS acceptance range; and
determining that weaning should continue if the FSP is higher than or equal to a minimum value of the FSP acceptance range, if PO2 exceeds a predefined value, if PCO2 is below a predefined value, and if VTMS exceeds a maximum value of the VTMS acceptance range.

63. The method of claim 52 further comprising
comparing FSP to an FSP acceptance range based on the determined optimal respiratory rate;
comparing VTMS to a VTMS acceptance range; and
determining that weaning should continue with increased level of controlled ventilation if VTMS is lower than a maximum value of the VTMS acceptance range, if PO2 exceeds a predefined value, if PCO2 is below a predefined value, and if FSP exceeds a maximum value of the FSP acceptance range.

64. The method of claim 52 further comprising
comparing FSP to an FSP acceptance range based on the determined optimal respiratory rate;
comparing VTMS to a VTMS acceptance range; and
determining that weaning should start, or should continue with a lowered level of controlled ventilation if started already, if FSP and VTMS are both within their respective acceptance ranges, if PO2 exceeds a predefined value, and if PCO2 is below a predefined value.

65. The method of claim 46 further comprising
comparing FSP to an FSP acceptance range based on the determined optimal respiratory rate;
comparing VTMS to a VTMS acceptance range; and
determining that weaning should start or continue with a lowered level of controlled ventilation if FSP and VTMS are both within their respective acceptance ranges.

66. The method of claim 46 further comprising
comparing FSP to an FSP acceptance range based on the determined optimal respiratory rate;
comparing VTMS to a VTMS acceptance range; and
determining that weaning should continue with an increased level of controlled ventilation if VTMS is below a maximum value of the VTMS acceptance range, if PO2 exceeds a predefined value, and if FSP exceeds a maximum value of the FSP acceptance range.

67. The method of claim 46 further comprising
comparing FSP to an FSP acceptance range based on the determined optimal respiratory rate;
comparing VTMS to a VTMS acceptance range; and
determining that weaning should continue if FSP is higher than or equal to a minimum value of the FSP acceptance range, if PO2 exceeds a predefined value, and if VTMS exceeds a maximum value of the VTMS acceptance range.

* * * * *

UNITED STATES PATENT AND TRADEMARK OFFICE
CERTIFICATE OF CORRECTION

PATENT NO.         : 8,695,593 B2
APPLICATION NO.    : 11/841806
DATED              : April 15, 2014
INVENTOR(S)        : Fleur T. Tehrani Page 1 of 1

It is certified that error appears in the above-identified patent and that said Letters Patent is hereby corrected as shown below:

In the Specification
In column 3, line 67, "Apparatus 111" should be "Apparatus 11"
In column 6, line 31, "ti" should be deleted
In column 6, line 66, "/-3.5" should be "+/-3.5"

In the Claims
In column 19, claim 55, line 51, "mm hg" should be "mm Hg"
Also an equation has been printed in a peculiar form in several places in the document (column 7, lines 34-39, column 15, claim 17, lines 38-44, column 16, claim 25, lines 25-30, column 19, claim 49, lines 1-6, column 20, claim 58, lines 1-6). Please correct the equation with the one below.

$$F1 = 60 \times \left[ \frac{-K' \times VD + \sqrt{(K' \times VD)^2 + 4 \times K' \times RES \times \Pi^2 \times (\frac{VALV}{60}) \times VD}}{2 \times RES \times \Pi^2 \times VD} \right]$$

Signed and Sealed this
Eighth Day of July, 2014

Michelle K. Lee
*Deputy Director of the United States Patent and Trademark Office*